United States Patent
Grönberg et al.

(10) Patent No.: US 10,431,326 B2
(45) Date of Patent: Oct. 1, 2019

(54) METHOD FOR INDICATING A PRESENCE OR NON-PRESENCE OF AGGRESSIVE PROSTATE CANCER

(71) Applicant: Phadia AB, Uppsala (SE)

(72) Inventors: Henrik Grönberg, Umeå (SE); Martin Eklund, Stockholm (SE)

(73) Assignee: PHADIA AB, Uppsala (SE)

( * ) Notice: Subject to any disclaimer, the term of this patent is extended or adjusted under 35 U.S.C. 154(b) by 563 days.

(21) Appl. No.: 14/443,970

(22) PCT Filed: Nov. 20, 2013

(86) PCT No.: PCT/EP2013/074259
§ 371 (c)(1),
(2) Date: May 19, 2015

(87) PCT Pub. No.: WO2014/079865
PCT Pub. Date: May 30, 2014

(65) Prior Publication Data
US 2015/0317431 A1    Nov. 5, 2015

(30) Foreign Application Priority Data

Nov. 20, 2012 (SE) ...................................... 1251312
May 16, 2013 (SE) ...................................... 1350600

(51) Int. Cl.
| | |
|---|---|
| C12Q 1/68 | (2018.01) |
| G01N 33/53 | (2006.01) |
| G16B 20/00 | (2019.01) |
| C12Q 1/6886 | (2018.01) |
| G01N 33/574 | (2006.01) |

(52) U.S. Cl.
CPC ........... *G16B 20/00* (2019.02); *C12Q 1/6886* (2013.01); *G01N 33/57434* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2011/0301863 A1 | 8/2011 | Auribault et al. |
| 2012/0021925 A1 | 1/2012 | Atnikov et al. |
| 2012/0150032 A1* | 6/2012 | Gudmundsson ..... C12Q 1/6886 600/437 |
| 2012/0202888 A1 | 8/2012 | Ma |
| 2015/0094221 A1 | 4/2015 | Grönberg et al. |
| 2015/0284804 A1 | 10/2015 | Grönberg et al. |

FOREIGN PATENT DOCUMENTS

| | | |
|---|---|---|
| WO | 03/100079 A2 | 12/2003 |
| WO | 2010/012823 A1 | 2/2010 |
| WO | 2010/081240 A1 | 7/2010 |
| WO | 2010/093939 A2 | 8/2010 |
| WO | 2011/150515 A1 | 12/2011 |
| WO | 2012/031207 A2 | 3/2012 |
| WO | 2013/172779 A2 | 11/2013 |
| WO | 2014/079874 A1 | 5/2014 |

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Official Action from European Application No. 13792689.5, dated Aug. 1, 2016.
Official Action from Chinese Application No. 201380069472.6, dated May 9, 2016, and English Translation.
Search Report from Chinese Application No. 201380069472.6, dated May 9, 2016, and English Translation.
Aly et al., Polygenic Risk Score Improves Prostate Cancer Risk Prediction: Results from the Stockholm-1 Cohort Study, European Urology, 60(1):21-28 (online Jan. 18, 2011).
Nordstrom et al., Comparison Between the Four-kallikrein Panel and Prostate Health Index for Predicting Prostate Cancer, European Urology, 68(1):139-146 (online Jul. 1, 2015).
Nordstrom et al., A Genetic Score Can Identify Men at High Risk for Prostate Cancer Among Men With Prostate-Specific Antigen of 1-3 ng/ml, European Urology 65:1184-1190 (online Jul. 19, 2013).
Nichol et al., Cost-effectiveness of Prostate Health Index for prostate cancer detection, BJU International, 110:353-362 (2011).
Brown et al., Macrophage Inhibitory Cytokine 1: A New Prognostic Marker in Prostate Cancer, Clin Cancer Res, 15 (21):1-7 (Nov. 1, 2009, online Oct. 20, 2009).
Klein et al., Blood Biomarker Levels to Aid Discovery of Cancer-Related Single-Nucleotide Polymorphisms: Kallikreins and Prostate Cancer, Cancer Prev Res, 3:611-619 (2010, Online First Apr. 27, 2010).
Shiiki et al., Association between saliva PSA and serum PSA in conditions with prostate adenocarcinoma, Biomarkers, 16(6):498-503 (2011).
Ewing et al., Germline Mutations in H0XB13 and Prostate-Cancer Risk, The New England Journal of Medicine, 366:141-9 (Jan. 12, 2012).

(Continued)

*Primary Examiner* — James Martinell
(74) *Attorney, Agent, or Firm* — Porter Wright Morris & Arthur LLP

(57) ABSTRACT

The present invention relates generally to the detection and identification of various forms of genetic markers, and various forms of proteins, which have the potential utility as diagnostic markers. By determining the level of a plurality of biomarkers and genetic markers in a patient sample, and combining the obtained values according to a predefined formula, it is possible to determine if it is likely that the patient suffers from aggressive prostate cancer. The present invention is particularly applicable only for patients having a body mass index value greater than 25.

19 Claims, 3 Drawing Sheets

(56) References Cited

OTHER PUBLICATIONS

Cybulski et al., A Novel Founder CHEK2 Mutation is Associated with Increased Prostate Cancer Risk, Cancer Res, 64:2677-2679 (2004).
Cybulski et al., NBS1 Is a Prostate Cancer Susceptibility Gene, Cancer Res, 64:1215-1219 (2004).
Thompson et al., Assessing Prostate Cancer Risk: Results from the Prostate Cancer Prevention Trial, Journal of the National Cancer Institute, vol. 98, No. 8, pp. 529-534 (Apr. 19, 2006).
Hastie et al., The Elements of Statistical Learning, Data Mining, Inference, and Prediction, Springer Series in Statistics, Second Edition (Aug. 2008), pp. vii-xxii.
Breiman, Random Forests, Machine Learning, 45:5-32 (2001).
Magi et al., Contribution of 32 GWAS-Identified Common Variants to Severe Obesity in European Adults Referred for Bariatric Surgery, Plos One, vol. 8, Issue 8, p. 1-9 (Aug. 7, 2013).
Song et al., Whole Milk Intake Is Associated with Prostate Cancer-Specific Mortality among U.S. Male Physicians, The Journal of Nutrition, 143:189-196 (2013, online Dec. 19, 2012).
Liu et al., A Replication Study Examining Three Common Single-Nucleotide Polymorphisms and the Risk of Prostate Cancer in a Japanese Population, The Prostate, 71:1023-1032 (2011, online Dec. 28, 2010).
Speliotes et al., Association analyses of 249,796 individuals reveal 18 new loci associated with body mass index, Nature Genetics, 42(11):937-948 (Nov. 2010).
Scardino, Peter T., Prostate cancer: Improving PSA testing by adjusting for genetic background, Nature Reviews Urology, 10:190-192 (Apr. 2013, online Feb. 19, 2013).
Moller et al., Lifetime body size and prostate cancer risk in a population-based case-control study in Sweden, Cancer Causes & Control, vol. 24, No. 12, p. 2143-2155 (online Sep. 19, 2013).
Johansson et al., Combining 33 genetic variants with prostate-specific antigen for prediction of prostate cancer: longitudinal study, International Journal of Cancer, vol. 130, No. 1, p. 129-137 (online Feb. 15, 2011).
Gudmundsson et al., Genetic Correction of PSA Values Using Sequence Variants Associated with PSA Levels, Science Translational Medicine, vol. 2, No. 62, p. 62ra92 (1-15) (Dec. 15, 2010).
Nam et al., Single Nucleotide Polymorphism of the Human Kallikrein-2 Gene Highly Correlates with Serum Human Kallikrein-2 Levels and in Combination Enhances Prostate Cancer Detection, Journal of Clinical Oncology, 21 (12):2312-9 (Jun. 15, 2003).
Vickers et al., Reducing Unnecessary Biopsy During Prostate Cancer Screening Using a Four-Kallikrein Panel: An Independent Replication, Journal of Clinical Oncology, vol. 28, No. 15, p. 2493-2498 (May 20, 2010).
Nordstrom et al., Prostate-specific Antigen (PSA) Testing Is Prevalent and Increasing in Stockholm County, Sweden, Despite No Recommendations for PSA Screening: Results from a Population-based Study, 2003-2011, European Association of Urology, 63:419-425 (online Oct. 12, 2012).
Anders Bjartell, Genetic Markers and the Risk of Developing Prostate Cancer, European Urology, 60:29-31 (Jan. 1, 2011).
Klein et al., Evaluation of Multiple Risk-Associated Single Nucleotide Polymorphisms Versus Prostate-Specific Antigen at Baseline to Predict Prostate Cancer in Unscreened Men, European Urology, 61:471-477 (online: Nov. 9, 2011).
Kader et al., Potential Impact of Adding Genetic Markers to Clinical Parameters in Predicting Prostate Biopsy Outcomes in Men Following an Initial Negative Biopsy: Findings from the REDUCE Trial, European Urology, 62:953-961 (online: May 11, 2012).
Choudhury et al., The Role of Genetic Markers in the Management of Prostate Cancer, European Urology, 62:577-587 (online: Jun. 5, 2012).
Official Action from European Application No. 13727408.0, dated Feb. 24, 2016.
Official Action from European Application No. 13792689.5, dated Mar. 21, 2016.
Breyer et al., Confirmation of the HOXB13 G84E Germline Mutation in Familial Prostate Cancer, Cancer Epidemiol Biomarkers Prev., 21(8):1348-1353 (Aug. 2012).
Lindstrom et al., Characterizing Associations and SNP-Environment Interactions for GWAS-Identified Prostate Cancer Risk Markers—Results from BPC3, PLoS ONE, vol. 6, Issue 2E17142, p. 1-11 (Feb. 2011).
Haiman et al., Genome-wide association study of prostate cancer in men of African ancestry identifies a susceptability locus at 17q21, Nat Genet., 43(6):570-573 (Jun. 2011).
Vickers et al., A panel of kallikrein markers can reduce unnecessary biopsy for prostate cancer: data from the European Randomized Study of Prostate Cancer Screening in Goteborg, Sweden, BMC Medicine, 6:19, pp. 1-10 (2008).
Ramirez et al., Beyond prostate-specific antigen: alternate serum markers, Prostate Cancer and Prostalic Diseases, 11:216-229 (2008).
Eeles et al., Identification of 23 new prostate cancer susceptibility loci using the iCOGS custom genotyping array, Nat Genet., 45(4):385-91 (Apr. 2013).
Sung Kyu Hong, Kallikreins as Biomarkers for Prostate Cancer, BioMed Research International, vol. 2014, ID 526341,pp. 1-10 (2014).
Kote-Jarai et al., Seven novel prostate cancer susceptibility loci identified by a multi-stage genome-wide association study, Nat Genet., vol. 43, No. 8, pp. 785-791 (2011).
Gudmundsson et al., Genome-wide association and replication studies identify four variants associated with prostate cancer susceptibility, Nat Genet., 41(10):1122-1126 (Oct. 2009).
Gudmundsson et al., Genetic correction of PSA values using sequence variants associated with PSA levels, Sci Transl Med., 2(62):62ra92 (Dec. 15, 2010).
Lindstrom et al., Replication of five prostate cancer loci identified in an Asian population—Results from the NCI Breast and Prostate Cancer Cohort Consortium (BPC3), Cancer Epidemiol Biomarkers Prev. 21(1):212-216 (Jan. 2012).
Schumacher et al., Genome-wide association study identifies new prostate cancer susceptibility loci, Human Molecular Genetics, vol. 20, No. 19, pp. 3867-3875 (Jul. 8, 2011).
Olama et al., A meta-analysis of genome-wide association studies to identify prostate cancer susceptibility loci associated with aggressive and non-aggressive disease, Human Molecular Genetics, 2013, vol. 22, No. 2, pp. 408-415 (2012).
Xu et al., Inherited genetic variant predisposes to aggressive but not indolent prostate cancer, Proceedings of the National Academy of Sciences, vol. 107, No. 5, p. 2136-2140 (Feb. 2, 2010).
Jin et al., Genome-wide copy-number variation analysis identifies common genetic variants at 20p13 associated with aggressiveness of prostate cancer, Carcinogenesis, 32(7):1057-1062 (May 5, 2011).
Hong, Kallikreins as Biomarkers for Prostate Cancer, BioMed Research International, vol. 2014, Article ID 526341, pp. 1-10 (2014).
Lim et al., Suseptibility variants for obesity and colorectal cancer risk: the multiethnic cohort and PAGE studies, Int J Cancer, 131(6):e1038-43 (Sep. 15, 2012).
Nguyen et al., Fatty acid synthase polymorphisms, tumor expression, body mass index, prostate cancer risk, and survival, J Clin Oncol, 1;28(25):3958-64 (Sep. 1, 2010), Abstract only.
Stark et al., Toll-like receptor signaling pathway variants and prostate cancer mortality, Cancer Epidemiol Biomarkers Prev., 18(6):1859-63 (Jun. 2009), Abstract only.
Gronberg et al., Prostate cancer screening in men aged 50 to 69 years (STHLM3): A prospective population-based diagnostic study, Urologic Oncology, 35:120-123 (2017), Abstract only.
Gronberg et al., Prostate cancer screening in men aged 50-69 years (STHLM3): a prospective population-based diagnostic study, Lancet Oncology, vol. 16, pp. 1667-1676 (Dec. 2015).
Lindmark et al., H6D Polymorphism in Macrophage-Inhibitory Cytokine-1 Gene Associated With Prostate Cancer, Journal of the National Cancer Institute, vol. 96, No. 16, pp. 1248-1254 (Aug. 18, 2004).
Official Action dated Nov. 20, 2013 from corresponding Russian Patent Application No. 2015124054, English Translation.

(56) References Cited

OTHER PUBLICATIONS

Official Action dated Oct. 24, 2017 from corresponding Japanese Patent Application No. 2015542308, English Translation.
Official Action dated Mar. 6, 2018 from corresponding European Patent Application No. 17210720.3.
Johnson et al., Genome-Wide Association Scan Identifies a Risk Locus for Preeclampsia on 2q14, Near the Inhibin, Beta B Gene, vol. 7, Issue 3, pp. 1-11 (Mar. 2012).
Examination report No. 1 for standard patent application dated Oct. 23, 2018 to corresponding Australian Application No. 2013349801.
Bjartell, Anders, Genetic Markers and the Risk of Developing Prostate Cancer, European Urology, vol. 60, pp. 29-31 (2011).
Klein, Robert J. et al., Evaluation of Multiple Risk-Associated Single Nucleotide Polymorphisms Versus Prostate-Specific Antigen at Baseline to Predict Prostate Cancer in Unscreened Men, European Urology, vol. 61, No. 3, pp. 471-477 (2011).
English Translation of Official Action dated Apr. 26, 2018 from corresponding Israeli Application No. 238724.
English Translation of Official Action dated 2018 from corresponding Russian application No. 2015124054.
English translation of Office Action dated Jan. 1, 2019 from corresponding Israeli Application No. 238724.

\* cited by examiner

METHOD FOR INDICATING A PRESENCE OR NON-PRESENCE OF AGGRESSIVE PROSTATE CANCER

FIELD OF THE INVENTION

The present invention relates generally to the detection and identification of various forms of genetic markers, and various forms of proteins, which have the potential utility as diagnostic markers. In particular, the present invention relates to the simultaneous use of multiple diagnostic markers for improved detection of aggressive forms of prostate cancer. More particularly, the present invention relates to the simultaneous use of multiple diagnostic markers for improved detection of aggressive prostate cancer for men that have a body mass index (BMI) above 25.

BACKGROUND OF THE INVENTION

The measurement of serum prostate specific antigen (PSA) is widely used for the screening and early detection of prostate cancer (PCa). As discussed in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein), serum PSA that is measurable by current clinical immunoassays exists primarily as either the free "non-complexed" form (free PSA), or as a complex with a-lantichymotrypsin (ACT). The ratio of free to total PSA in serum has been demonstrated to significantly improve the detection of PCa. Other factors, like age and documented family history may also improve the detection of PCa further. The measurement of genetic markers related to PCa, in particular single nucleotide polymorphisms (SNP), is an emerging modality for the screening and early detection of prostate cancer. Analysis of multiple PCa related SNPs can, in combination with biomarkers like PSA and with general information about the patient improve the risk assessment through a combination of several SNPs into a genetic score.

The screening and early detection of prostate cancer is a complicated task, and to date no single biomarker has been proven sufficiently good for specific and sensitive mapping of the male population. Therefore, attempts have been spent on combining biomarker levels in order to produce a formula which performs better in the screening and early detection of PCa. The most common example is the regular PSA test, which in fact is an assessment of "free" PSA and "total" PSA. PSA exists as one "non-complex" form and one form where PSA is in complex formation with alpha-lantichymotrypsin. Another such example is the use of combinations of concentrations of free PSA, total PSA, and one or more pro-enzyme forms of PSA for the purpose of diagnosis, as described in WO03100079 (METHOD OF ANALYZING PROENZYME FORMS OF PROSTATE SPECIFIC ANTIGEN IN SERUM TO IMPROVE PROSTATE CANCER DETECTION) which is incorporated by reference herein. The one possible combination of PSA concentrations and pro-enzyme concentrations that may result in improved performance for the screening and early detection of PCa is the phi index. Phi was developed as a combination of PSA, free PSA, and a PSA precursor form [−2]proPSA to better detecting PCa for men with a borderline PSA test (e.g. PSA 2-10 ng/mL) and non-suspicious digital rectal examination, as disclosed in the report "Cost-effectiveness of Prostate Health Index for prostate cancer detection" by Nichol M B and co-authors as published in BJU Int. 2011 Nov. 11. doi: 10.1111/j.1464-410X.2011.10751.x. which is incorporated by reference herein. Another such example is the combination of psp94 and PSA, as described in US2012021925 (DIAGNOSTIC ASSAYS FOR PROSTATE CANCER USING PSP94 AND PSA BIOMARKERS).

There are other biomarkers of potential diagnostic or prognostic value for assessing if a patient suffers from PCa, including MIC-1 as described in the report "Macrophage Inhibitory Cytokine 1: A New Prognostic Marker in Prostate Cancer" by David A. Brown and co-authors as published in Clin Cancer Res 2009; 15(21):OF1-7, which is incorporated by reference herein.

Attempts to combine information from multiple sources into one algorithmic model for the prediction of PCa risk has been disclosed in the past. In the public report "Blood Biomarker Levels to Aid Discovery of Cancer-Related Single-Nucleotide Polymorphisms: Kallikreins and Prostate Cancer" by Robert Klein and co-authors as published in Cancer Prev Res (2010), 3(5):611-619 (which is incorporated by reference herein), the authors discuss how blood biomarkers can aid the discovery of novel SNP, but also suggest that there is a potential role for incorporating both genotype and biomarker levels in predictive models. Furthermore, this report provides evidence that the non-additive combination of genetic markers and biomarkers in concert may have predictive value for the estimation of PCa risk. Later, Xu and co-inventors disclosed a method for correlating genetic markers with high grade prostate cancer, primarily for the purpose of identifying subjects suitable for chemopreventive therapy using 5-alpha reductase inhibitor medication (e.g. dutasteride or finasteride) in the patent application WO2012031207 (which is incorporated by reference herein). In concert, these two public disclosures summarizes the prior art of combining genetic information and biomarker concentration for the purpose of estimating PCa risk, also for high grade cancers.

The current performance of the PSA screening and early detection is approximately a sensitivity of 80% and specificity of 30%. It is estimated that approximately 65% will undergo unnecessary prostate biopsy and that 15-20% of the clinically relevant prostate cancers are missed in the current screening. In the United States alone, about 1 million biopsies are performed every year, which results in about 192 000 new cases being diagnosed. Hence, also a small improvement of diagnostic performance will result both in major savings in healthcare expenses due to fewer biopsies and in less human suffering from invasive diagnostic procedures.

The current clinical practice (in Sweden) is to use total PSA as biomarker for detection of asymptomatic and early prostate cancer. The general cutoff value for further evaluation with a prostate biopsy is 3 ng/mL. However, due to the negative consequences of PSA screening there is no organized PSA screening recommended in Europe or North America today.

It is particularly important to accurately identify aggressive prostate cancer (aPCa) in individuals because the sooner an individual is provided treatment, the greater likelihood of the cancer being cured. The identification of aPCa is however difficult, partly because larger cohorts are required to provide a sufficient number of cases and controls in the development of statistical models. Hence, the availability of predictive models for aPCa is low. This invention provides, however, predictive models for the identification of aPCa through analysis of biomarkers and genetic profile of an individual.

SUMMARY OF THE INVENTION

The present invention is based on the discovery that the combination of diagnostic markers of different origin may improve the ability to detect aPCa in a general population. In particular, the present invention improves the ability to detect aPCa in individuals having high body-mass index (BMI). This can result in major savings for the society, because aggressive cancers that are identified early are more easily treatable.

Accordingly, based on the discoveries of the present invention, one aspect of the present invention provides a method based on a redundantly designed combination of data for indicating the presence or non-presence of aggressive prostate cancer (PCa) in an individual, comprising the steps of:

1. Providing at least one biological sample from said individual;
2. In said biological sample, analyzing
   a. a category of PCa biomarkers, by measuring a presence or concentration of each of a plurality of PCa related biomarkers of said category of PCa biomarkers;
   b. a category of SNPs related to PCa (SNPpc), by measuring a presence or absence of each of a plurality of SNPpc of said category of SNPpc;
3. Combining data regarding said category of PCa biomarkers, to form a biomarker composite value representing the PCa biomarker-related risk of developing PCa;
4. Combining data regarding said category of SNPpc, to form a SNPpc composite value representing the SNPpc-related risk of developing PCa, wherein the method allows disregarding a subset of at least 5% of the SNPpc of the SNPpc category when forming the SNPpc composite value;
5. Combining the biomarker composite value and the SNPpc composite value, to form an overall composite value;
6. Correlating said overall composite value to the presence or non-presence of aggressive PCa in said individual by comparing said overall composite value to a pre-determined cut-off value established with control samples of known aggressive PCa and benign disease diagnosis.

According to an aspect of the invention, one or more of the method steps, typically steps 3, 4, 5 and/or 6, are provided by means of a computer program product when executed in a computer comprising a processor and memory.

Typically, step 3 of the above-described method is conducted with a computer programmed to form or calculate a biomarker composite value from the data of step 2a; step 4 of the above-described method is conducted with a computer programmed to form or calculate a SNPpc composite value from the data of step 2b; step 5 is conducted with a computer programmed to form or calculate an overall composite value from the data of steps 3 and 4; and/or step 6 of the above-described method is conducted with a computer programmed to correlate the overall composite value to the presence or non-presence of aggressive PCa in said individual by comparing said overall composite value to a pre-determined cut-off value established with control samples of known aggressive PCa and benign disease diagnosis. Additionally, the present invention relates to a non-transitory, tangible computer readable storage medium having executable instructions to conduct such calculations or form such composite values and/or to conduct the correlation step as described above.

The choice of cut-off value (or cut-off level) depends on many factors, including but not limited to the risk of the disease as such and the risk associated with inaccurately diagnosing an individual as positive who do not have the disease (false positive). The choice of cut-off value is described more in detail further below.

In a preferred embodiment of the invention, step 2(a) of the above method comprises measuring the presence or concentration of at least partially redundant PCa biomarkers, and wherein at least one, such as two, of the PCa biomarkers is selected from the group consisting of (i) PSA, (ii) total PSA (tPSA), (iii) intact PSA (iPSA), (iv) free PSA (IPSA), and (v) hK2.

More particularly, the method allows disregarding a subset of at least one of said PCa biomarkers (i)-(v) of the PCa biomarker category when forming said biomarker composite value, such as a subset of one, two, three, or four of said PCa biomarkers (i)-(v).

Further, in an embodiment, the above method allows disregarding at least 10%, such as 15%, such as 20%, such as 30% of the SNPpc of the SNPpc category when forming the SNPpc composite value.

Preferably, the data regarding the category of PCa biomarkers are combined according to a predetermined equation to form said biomarker composite value, and/or the data regarding the category of SNPpc are combined according to a predetermined equation to form said SNPpc composite value. Also, said biomarker composite value and said SNPpc composite value are preferably combined according to a predetermined equation to form said overall composite value.

In an embodiment, the above method further comprises a step of recommending the individual for biopsy if the overall composite value is greater than the cut-off value.

In yet an embodiment, the above method further comprises a step of recommending the individual to change dietary habits, to lose weight, to reach a BMI value below 30, to exercise regularly, and/or to stop smoking, if the overall composite value is greater than the cut-off value.

In an embodiment of the present invention, the SNP related to PCa (SNPpc) include at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, rs2405942, rs12621278, rs9364554, rs10486567, rs6465657, rs2928679, rs6983561, rs16901979, rs16902094, rs12418451, rs4430796, rs11649743, rs2735839, rs9623117, and rs138213197.

In an embodiment, the method further comprises analyzing a category of SNP related to a PCa biomarker concentration (SNPbm), by measuring a presence or absence of at least one SNPbm; combining data regarding said SNPbm to form a SNPbm composite value, and including said SNPbm composite value in said overall composite value.

In an embodiment, the at least one SNPbm includes at least one of rs3213764, rs1354774, rs1227732, rs2736098, rs401681, rs10788160, rs11067228, rs1363120, rs888663, and rs1054564.

In an embodiment of the invention, the method further comprises analyzing a category of SNP related to the Body Mass Index of said individual (SNPbmi), by measuring a presence or absence of at least one SNPbmi; combining data regarding said SNPbmi to form a SNPbmi composite value; and including said SNPbmi composite value in said overall composite value.

In an embodiment, the at least one SNPbmi includes at least one of rs3817334, rs10767664, rs2241423, rs7359397, rs7190603, rs571312, rs29941, rs2287019, rs2815752, rs713586, rs2867125, rs9816226, rs10938397, and rs1558902.

In another embodiment of the invention, the method further comprises collecting the family history regarding PCa, treatment history, and physical data from said individual; and wherein said family history, treatment history and/or physical data are included in the combined data forming said overall composite value.

In yet another embodiment of the invention, the method further comprises analyzing an additional category of PCa biomarkers, by measuring the presence or concentration of one or each of a plurality of PCa biomarkers of said additional biomarker category; combining data regarding said additional PCa biomarker category to form an additional biomarker composite value for said additional PCa biomarker category; and including said additional biomarker composite value in the overall composite value; wherein the combination of data to form the additional biomarker composite value is redundantly designed where the additional category of PCa biomarkers comprises more than one PCa biomarker.

In a preferred embodiment, the additional category of PCa biomarkers comprises the biomarker MIC-1 and optionally other MIC-1 related biomarkers, or the biomarker MSMB and optionally other MSMB related biomarkers.

In another embodiment, the method comprises analyzing each of a plurality of additional categories of PCa biomarkers and forming an additional biomarker composite value for each of the PCa biomarker categories, according to the above-described procedure. Preferably, at least two additional categories of PCa biomarkers are analyzed, wherein one additional category of PCa biomarkers comprises the biomarker MIC-1 and optionally other MIC-1 related biomarkers, and another additional category comprises the biomarker MSMB and optionally other MSMB related biomarkers.

In an embodiment, the biological sample is a blood sample.

In an embodiment of the invention, the overall composite value is calculated using a method in which the non-additive effect of a SNP related to a PCa biomarker concentration (SNPbm) and the corresponding PCa biomarker concentration is utilized.

In a preferred embodiment of the method according to the present invention, the individual has a BMI value greater than 25, such as greater than 30.

In an embodiment of the method, the measurement of the presence or absence of SNPs is conducted by use of MALDI mass spectrometry.

In an embodiment of the method, the measurement of a presence or concentration of PCa biomarkers is conducted by use of microarray technology.

In a preferred embodiment of the method, the measurement of a presence or absence of a SNP (belonging to any category of SNPs) comprises measuring the number of alleles of said SNP. In an embodiment, one or two alleles corresponds to a presence of said SNP and zero alleles corresponds to an absence of said SNP in said individual; wherein zero alleles corresponds to homozygous negative for said SNP, one allele corresponds to heterozygous positive, and two alleles corresponds to homozygous positive.

In an embodiment, the above-described method comprises using an ELISA assay device, a microarray assay device, an immunoprecipitation assay device, an immunofluorescence assay device, a radio-immuno-assay device, or a mass spectrometry device using matrix-assisted laser desorption/ionization (MALDI), for the measurement of a presence or concentration of a PCa biomarker.

In an embodiment, which may be combined with the above-mentioned embodiment, the above-described method comprises using a mass spectrometry device using matrix-assisted laser desorption/ionization (MALDI), for the measurement of a presence or absence of a SNP.

Another aspect of the present invention provides an assay device for performing step 2a (i.e. measuring a presence or concentration of at least one PCa biomarker) and step 2b (i.e. measuring a presence or absence of at least one SNPpc) of the above-described method for indicating a presence or non-presence of aggressive prostate cancer in an individual, said assay device comprising a solid phase having immobilised thereon at least two different categories of ligands, wherein:

the first category of said ligands binds specifically to a PCa biomarker, and includes a plurality of different ligands binding specifically to each of a plurality of different PCa biomarkers, preferably at least one of PSA, iPSA, tPSA, fPSA, hK2, and optionally MSMB and/or MIC-1; and the second category of said ligands binds specifically to a SNPpc, and includes a plurality of different ligands binding specifically to each of a plurality of different SNPpc, such as at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment, the assay device is further adapted for measuring a presence or absence of a SNPbm, in which case the solid phase of the assay device further has a third category of ligand immobilized which binds specifically to a SNPbm, and includes one or a plurality of different ligands binding specifically to one or each of a plurality of different SNPbm, such as at least one of rs1227732, rs3213764, rs1354774, rs2736098, rs401681, rs10788160, rs11067228, rs1363120, rs888663, and rs1054564.

In an embodiment, the assay device is adapted for measuring a presence or absence of a SNPbmi, in which case the solid phase further has a fourth category of ligand immobilized which binds specifically to a SNPbmi, and includes one or a plurality of different ligands binding specifically to one or a plurality of different SNPbmi, such as at least one of rs3817334, rs10767664, rs2241423, rs7359397, rs7190603, rs571312, rs29941, rs2287019, rs2815752, rs713586, rs2867125, rs9816226, rs10938397, and rs1558902.

In an embodiment, the above-described assay device comprises an ELISA assay device, a microarray assay device, an immunoprecipitation assay device, an immunofluorescence assay device, a radio-immuno-assay device, or a mass spectrometry device using matrix-assisted laser desorption/ionization (MALDI), for the measurement of a presence or concentration of a PCa biomarker.

In an embodiment, which may be combined with the above-mentioned embodiment, the above-described assay device comprises a mass spectrometry device using matrix-assisted laser desorption/ionization (MALDI), for the measurement of a presence or absence of a SNP.

According to a further aspect of the invention, a test kit is provided for performing step 2a (i.e. measuring a presence or concentration of at least one PCa biomarker) and step 2b (i.e. measuring a presence or absence of at least one SNPpc) of the above-described method for indicating a presence or non-presence of aggressive prostate cancer in an individual, comprising a corresponding assay device as described above and at least two categories of detection molecules, wherein:
the first category of said detection molecules is capable of detecting a PCa biomarker, preferably at least one of PSA, iPSA, tPSA, fPSA, and hK2, and optionally MSMB and/or MIC-1; and
the second category of said detection molecules is capable of detecting a SNPpc, such as at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment, the test kit comprises an assay device that is further adapted for measuring a presence or absence of at least one SNPbm, and a third category of detection molecule, which is capable of detecting a SNPbmi, such as at least one of rs1227732, rs3213764, rs1354774, rs2736098, rs401681, rs10788160, rs11067228, rs1363120, rs888663, and rs1054564.

In an embodiment, the test kit comprises an assay device that is adapted for measuring a presence or absence of a SNPbmi, and a fourth category of detection molecule, which is capable of detecting a SNPbmi, such as at least one of rs3817334, rs10767664, rs2241423, rs7359397, rs7190603, rs571312, rs29941, rs2287019, rs2815752, rs713586, rs2867125, rs9816226, rs10938397, and rs1558902.

Yet another aspect of the present invention provides an assay device comprising a solid phase having immobilised thereon at least two different categories of ligands, wherein:
the first category of said ligands binds specifically to a PCa biomarker, and includes a plurality of different ligands binding specifically to each of a plurality of different PCa biomarkers selected from at least one of PSA, iPSA, tPSA, fPSA, and hK2, and optionally MSMB and/or MIC-1; and
the second category of said ligands binds specifically to a SNPpc, and includes a plurality of different ligands binding specifically to each of a plurality different SNPpc, selected from at least one of rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, or rs2405942, rs12621278, rs9364554, rs10486567, rs6465657, rs2928679, rs6983561, rs16901979, rs16902094, rs12418451, rs4430796, rs11649743, rs2735839, rs9623117 and rs138213197.

In an embodiment of the assay device, the solid phase further has a third category of ligand immobilised, which binds specifically to a SNPbm, and including one or a plurality of different ligands binding specifically to one or each of a plurality of different SNPbm selected from at least one of rs1227732, rs3213764, rs1354774, rs2736098, rs401681, rs10788160, rs11067228, rs1363120, rs888663, and rs1054564.

In a further embodiment of the assay device, the solid phase further has a fourth category of ligand immobilised, which binds specifically to a SNPbmi, and including one or a plurality of different ligands binding specifically to one or each of a plurality of different SNPbmi selected from at least one of rs3817334, rs10767664, rs2241423, rs7359397, rs7190603, rs571312, rs29941, rs2287019, rs2815752, rs713586, rs2867125, rs9816226, rs10938397, and rs1558902.

Yet another aspect of the invention provides a computer program product directly loadable into the internal memory of a digital computer, wherein the computer program product comprises software code means for performing at least step 3 (i.e. combining data regarding said category of PCa biomarkers to form a biomarker composite value), step 4 (i.e. combining data regarding said category of SNPpc to form a SNPpc composite value), step 5 (i.e. combining the biomarker composite value and the SNPpc composite value to form an overall composite value), and/or step 6 (correlating said overall composite value to the presence or non-presence of aggressive PCa in said individual by comparing the overall composite value to a pre-determined cut-off value established with control samples of known aggressive PCa and benign disease diagnosis) of the above-described method for indicating a presence or non-presence of aggressive prostate cancer in an individual; such as step 1 (i.e. providing at least one biological sample from said individual), step 2 (in the biological sample, analysing a category of PCa biomarkers by measuring a presence or concentration of each of a plurality of PCa biomarkers, and analyzing a category of SNPpc by measuring a presence or absence of each of a plurality of SNPpc), steps 3, 4, 5 and 6 of said method.

In an embodiment, the computer program product further comprises software code means for analyzing a category of SNPbm by measuring a presence or absence of at least one SNPbm.

In another embodiment, the computer program product further comprises software code means for analyzing a category of SNPbmi by measuring a presence or absence of at least one SNPbmi.

A further aspect of the invention provides an apparatus comprising an assay device as described above and a corresponding computer program product as described above.

DETAILED DESCRIPTION OF THE INVENTION

Figure 1:
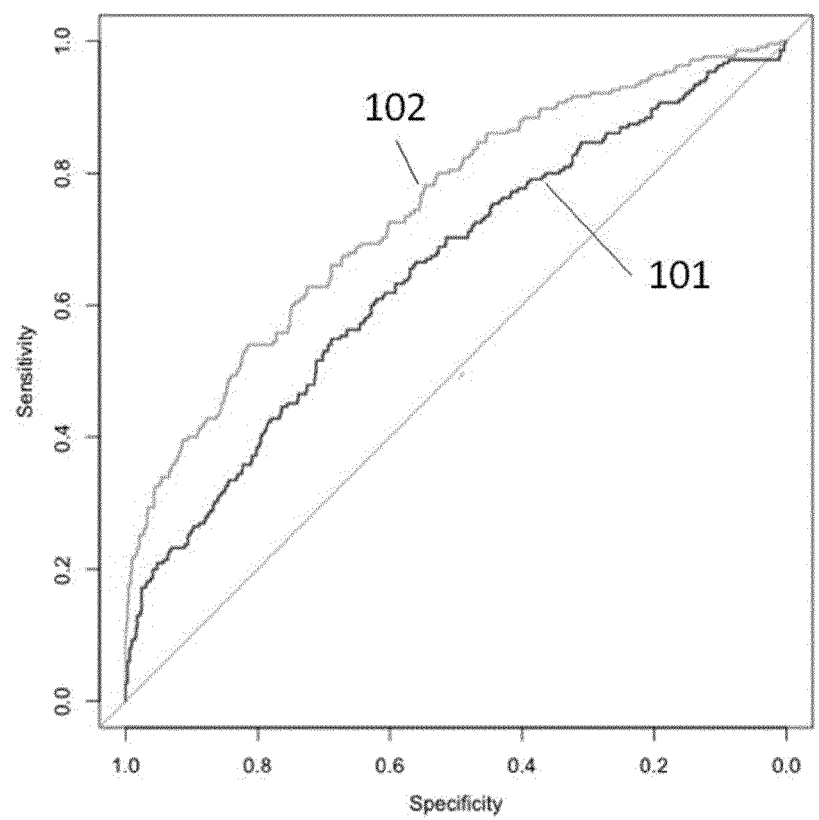
FIG. 1 shows the ROC curves for the linear model of Example 1 illustrating the difference in performance between PSA (101) and a multiparametric model (102) in prediction of aPCa.

For the purpose of this application and for clarity, the following definitions are made:

The term "PSA" refers to serum prostate specific antigen in general. PSA exists in different forms, where the term "free PSA" refers to PSA that is unbound or not bound to another molecule, the term "bound PSA" refers to PSA that is bound or complexed to another molecule, and finally the term "total PSA" refers to the sum of free PSA and bound (complexed) PSA. The term "FIT PSA" is the ratio of unbound PSA to total PSA. There are also molecular derivatives of PSA, where the term "proPSA" refers to a precursor inactive form of PSA and "intact PSA" refers to an additional form of proPSA that is found intact and inactive.

The term "diagnostic assay" refers to the detection of the presence or nature of a pathologic condition. It may be used interchangeably with "diagnostic method". Diagnostic assays differ in their sensitivity and specificity.

One measure of the usefulness of a diagnostic tool is "area under the receiver—operator characteristic curve", which is commonly known as ROC-AUC statistics. This widely accepted measure takes into account both the sensitivity and specificity of the tool. The ROC-AUC measure typically ranges from 0.5 to 1.0, where a value of 0.5 indicates the tool has no diagnostic value and a value of 1.0 indicates the tool has 100% sensitivity and 100% specificity.

The term "sensitivity" refers to the proportion of all subjects with PCa that are correctly identified as such (which is equal to the number of true positives divided by the sum of the number of true positives and false negatives).

The term "specificity" refers to the proportion of all subjects healthy with respect to PCa (i.e. not having PCa) that are correctly identified as such (which is equal to the number of true negatives divided by the sum of the number of true negatives and false positives).

The term "biomarker" refers to a protein, a part of a protein, a peptide or a polypeptide, which may be used as a biological marker, e.g. for diagnostic purposes.

The term "kallikrein-like biomarker" refers to protein biomarkers belonging to or being related to the kallikrein family of proteins, including but not limited to Prostate-specific antigen (PSA) in either free form or complexed form, pro PSA (a collection of isoforms of PSA) and in particular the truncated form (−2) pro PSA, intact PSA, human prostatic acid phosphatase (PAP), and human kallikrein 2 (abbreviated hK2 or HK2 or hk2 in the present application).

The term "single nucleotide polymorphism" (SNP) refer to the genetic properties of a defined locus in the genetic code of an individual. A SNP can be related to increased risk for PCa, and can hence be used for diagnostic or prognostic assessments of an individual. The Single Nucleotide Polymorphism Database (dbSNP) is an archive for genetic variation within and across different species developed and hosted by the National Center for Biotechnology Information (NCBI) in collaboration with the National Human Genome Research Institute (NHGRI), both located in the US. Although the name of the database implies a collection of one class of polymorphisms only (i.e., single nucleotide polymorphisms (SNP)), it in fact contains a range of molecular variation. Every unique submitted SNP record receives a reference SNP ID number ("rs#"; "refSNP cluster"). In this application, SNP are mainly identified using rs# numbers. Accordingly, within the present application, SNP is used to refer to the range of molecular variation as included in the dbSNP, rather than only single nucleotide polymorphisms. For the purpose of the present application, the terms "SNP" and "SNPs" may be used interchangeably, and may be used to describe the singular and/or the plural of "single nucleotide polymorphism".

The term "body-mass index" (BMI) refers to a heuristic proxy for human body fat based on an individual's weight and height, according to the formula BMI=weight/(height*height), where weight is the weight of an individual expressed in kilograms and height is the height of an individual expressed in meters. A normal healthy BMI value is typically considered to be within the range of 18.5 to 25, and individuals having BMI>30 are typically considered obese.

The term "aggressive prostate cancer" (aPCa) refers to a more serious condition than the average prostate cancer disease. aPCa can be defined in different ways, including but not limited to (a) prostate cancer of Gleason Score 7 or higher, (b) prostate cancer in tumor stage three or greater, (c) prostate cancer in an individual having a PSA value greater than 10 ng/mL, (d) an individual having an increasing PSA value (doubling time less than one year), and (e) computer assisted image analysis (e.g. positron emission tomography (PET) or single photon emission computerized tomography (SPECT) or computerized x-ray tomography (CT) or magnetic resonance imaging (MRI) or ultrasound imaging or any other computer assisted image analysis) indicating a tumor size in the higher quartile of the patient population.

The term "medical history" refers to information related to historic examinations, diagnoses and/or therapy for any cancer disease. One non-limiting example of medical history is if a subject has been examined for the presence of PCa previously through biopsy of the prostate.

The term "parameter category" refers to a group or a family of related parameters, such as related biomarkers or related SNPs, which are partly or completely redundant in terms of predictive performance. One example of a parameter category is "kallikrein-like biomarkers", a category which includes for example PSA, total PSA (tPSA), intact PSA (iPSA), free PSA (fPSA), and hk2. Another example of a parameter category is "SNP related to BMI", a category which includes SNPs that are related to the BMI of an individual. In the prediction models of the present invention, it may be sufficient to have measurement results (data) for a subset of the members of each category, so as to make each category represented in the prediction model, albeit using only a subset of the members of the respective categories. The term "parameter category" is sometimes referred to as only "category" in the present application.

The term "composite value" refers to the combination of data related to a parameter category into a representative value for said parameter category. The combination of data can typically be performed according to one or more predetermined equations. A composite value is the output of the combination of data according to one or more predetermined equations. The different equations are applicable for different measurement results (i.e. data), depending on for which subsets of the members of the parameter category that data are available. One non-limiting example of a method to form a composite value for a particular parameter category is to use the average of the available results for the members of said category. The term "composite value" is sometimes referred to as "score" in the present application. One non-limiting example of a composite value is "biomarker composite value". Another non-limiting example of a composite value is "genetics composite value" (or "genetic score"), and more specifically "SNP composite value".

The term "redundantly designed combination of data" refers to a combination of data obtained by a plurality of measurements, to form a composite value for one or more parameter categories or subsets thereof, wherein the combination of data is performed such that a composite value representing one parameter category can be produced based either on a subset of data for said category, e.g. where some data are missing or erroneous, or on the full set of data for said category.

The term "a plurality" as used in the present application means "two or more".

The present invention provides diagnostic methods to aid in indicating, estimating, detecting and/or determining the presence or non-presence of aggressive prostate cancer in a subject. The present invention can, if desired, be tailored to defined subpopulations in order to increase the performance and the usefulness of the invention within said subpopulation. Even though the present invention can be applied to the general population of male individuals, it is possible to construct diagnostic methods for the detection of aPCa with enhanced performance for defined subpopulations. One non-limiting example of a defined subpopulation is individuals having high body-mass index (BMI), for example BMI>25, or BMI>30 or BMI>35. Another non-limiting example of a defined subpopulation is individuals having low PSA value, for example PSA<4 ng/mL or PSA<3 ng/mL or PSA<2 ng/mL or PSA<1 ng/mL.

The basic principle of the invention is the use of combinations of biomarkers and genetic information in such a manner that the combinatorial use of the assessed information about the individual improves the quality of the diagnosis.

- Collecting the family history regarding PCa from said patient (Category HIST).
- Collecting patient physical data, such as weight, BMI, age and similar (Category PPD)
- Obtaining a number of biological samples from said patient.
- In said biological samples, measuring or quantifying the presence or concentration of a plurality of defined biomarkers (Category Biomarker), followed by combining data regarding said biomarkers to form a biomarker composite value.
- In said biological samples, measuring or quantifying the genetic status of said patients with respect to a plurality of defined SNPs related to PCa (Category SNPpc), by measuring or quantifying the presence or absence of a plurality of defined SNPs related to PCa (SNPpc), and followed by combining data obtained regarding the SNPs related to PCa, to form a SNPpc composite value.
- In said biological samples, measuring or quantifying the genetic status of said patients with respect to a plurality of defined SNPs related to biomarker expression level or biomarker concentration (Category SNPbm), by measuring or quantifying the presence or absence of a plurality of defined SNPs related to biomarker expression level or biomarker concentration (SNPbm), to form a SNPbm composite value.
- In said biological samples, measuring or quantifying the genetic status of said patients with respect to a plurality of defined SNPs related to the Body Mass Index (BMI) of said individual (Category SNPbmi), by measuring or quantifying the presence or absence of a plurality of defined SNPs related to BMI (SNPbmi), to form a SNPbmi composite value.
- Combining data from at least two of the categories defined above to form an overall composite value for the use in the detection of early aggressive prostate cancer.
- Determining by using said overall composite value, alone or in combination with further data, if the patient is likely to suffer from aPCa.

In more detail, the step comprising the collection of family history includes, but is not limited to, the identification of if any closely related male family member (such as the father, brother or son of the patient) suffers or have suffered from PCa.

Physical information regarding the patient is typically obtained through a regular physical examination wherein age, weight, height, BMI and similar physical data are collected.

Collecting biological samples from a patient includes, but is not limited to plasma, serum, DNA from peripheral white blood cells and urine.

The quantification of presence or concentration of biomarkers in a biological sample can be made in many different ways. One common method is the use of enzyme linked immunosorbent assays (ELISA) which uses antibodies and a calibration curve to assess the presence and (where possible) the concentration of a selected biomarker. ELISA assays are common and known in the art, as evident from the publication "Association between saliva PSA and serum PSA in conditions with prostate adenocarcinoma." by Shiiki N and co-authors, published in Biomarkers. 2011 September; 16(6):498-503, which is incorporated by reference herein. Another common method is the use of a microarray assay for the quantification of presence or concentration of biomarkers in a biological sample. A typical microarray assay comprises a flat glass slide onto which a plurality of different capture reagents (typically an antibody) each selected to specifically capture one type of biomarker is attached in non-overlapping areas on one side of the slide. The biological sample is allowed to contact, for a defined period of time, the area where said capture reagents are located, followed by washing the area of capture reagents. At this point, in case the sought-after biomarker was present in the biological sample, the corresponding capture reagent will have captured a fraction of the sought-after biomarker and keep it attached to the glass slide also after the wash. Next, a set of detection reagents are added to the area of capture reagents (which now potentially holds biomarkers bound), said detection reagents being capable of (i) binding to the biomarker as presented on the glass slide and (ii) producing a detectable signal (normally through conjugation to a fluorescent dye). It is typically required that one detection reagent per biomarker is added to the glass slide. There are many other methods capable of quantifying the presence or concentration of a biomarker, including, but not limited to, immunoprecipitation assays, immunofluorescence assays, radio-immuno-assays, and mass spectrometry using matrix-assisted laser desorption/ionization (MALDI), to mention a few examples.

The quantification of presence of SNPs through the analysis of a biological sample typically involves MALDI mass spectrometry analysis based on allele-specific primer extensions, even though other methods are equally applicable. This applies to any type of SNP, i.e. both SNPs related to PCa (SNPpc), SNPs related to the BMI (SNPbmi), and SNPs related to biomarker expression/concentration (SNPbm).

The combination of data can be any kind of algorithmic combination of results, such as a linear combination of data wherein the linear combination improves the diagnostic performance (for example as measured using ROC-AUC). Another possible combination includes a non-linear polynomial relationship.

Suitable biomarkers for diagnosing aPCa include, but are not limited to, Prostate-specific antigen (PSA) in either free form or complexed form, pro PSA (a collection of isoforms of PSA) and in particular the truncated form (−2) pro PSA, intact PSA, human prostatic acid phosphatase (PAP), human kallikrein 2 (hK2), early prostate cancer antigen (EPCA), Prostate Secretory Protein (PSP94; also known as beta-microseminoprotein and MSMB), glutathione S-transferase π(GSTP1), and α-methylacyl coenzyme A racemase (AMACR). Related biomarkers, which may be useful for improving the diagnostic accuracy of the method includes Macrophage Inhibitory Cytokine 1 (MIC-1; also known as GDF-15).

Suitable SNPs related to PCa include, but are not limited to rs12621278 (Chromosome 2, locus 2q31.1), rs9364554 (Chromosome 6, locus 6q25.3), rs10486567 (Chromosome 7, locus 7p15.2), rs6465657 (Chromosome 7, locus 7q21.3), rs2928679 (Chromosome 8, locus 8p21), rs6983561 (Chromosome 8, locus 8q24.21), rs16901979 (Chromosome 8, locus 8q24.21), rs16902094 (Chromosome 8, locus 8q24.21), rs12418451 (Chromosome 11, locus 11q13.2), rs4430796 (Chromosome 17, locus 17q12), rs11649743 (Chromosome 17, locus 17q12), rs2735839 (Chromosome 19, locus 19q13.33), rs9623117 (Chromosome 22, locus 22q13.1), and rs138213197 (Chromosome 17, locus 17q21)

Suitable SNPs related to PCa further include, but are not limited to rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, and rs2405942.

Suitable SNPs related to PCa further include, but are not limited to rs138213197 as described in the report "Germline mutations in HOXB 13 and prostate-cancer risk." by Ewing C M and co-authors as published in N Engl J Med. 2012 Jan. 12; 366(2):141-9 (which is incorporated by reference herein), 1100delC (22q12.1) and I157T (22q12.1) as described in the report "A novel founder CHEK2 mutation is associated with increased prostate cancer risk." by Cybulski C and co-authors as published in Cancer Res. 2004 Apr. 15; 64(8):2677-9 (which is incorporated by reference herein), and 657del5 (8q21) as described in the report "NBS 1 is a prostate cancer susceptibility gene" by Cybulski C and co-authors as published in Cancer Res. 2004 Feb. 15; 64(4):1215-9 (which is incorporated by reference herein).

It is possible to define a parameter category as "SNP related to PCa" which includes SNP related to PCa. Suitable members include (but are not limited to) the SNPs listed above. A subset of the members of this category would be sufficient to represent the category as such in a predictive model.

Suitable SNPs related to other processes than PCa include, but are not limited to rs3213764, rs1354774, rs2736098, rs401681, rs10788160, rs11067228, all being related to the expression level of PSA. It is possible to define a parameter category as "SNP related to concentration of PSA" or "SNP related to expression level of PSA", which includes SNP related to the concentration or expression level of PSA. A subset of the members of this category would be sufficient to represent the category as such in a predictive model. The SNP rs3213764 and rs1354774 relate particularly to the expression level of free PSA.

Suitable SNPs related to other processes than PCa further include, but are not limited to rs1363120, rs888663, rs1227732, rs1054564, all being related to the expression level of the inflammation cytokine biomarker MIC1. It is possible to define a parameter category as "SNP related to concentration of MIC1" or "SNP related to expression level of MIC1" which includes SNP related to the concentration or expression level of MIC1. A subset of the members of this category would be sufficient to represent the category as such in a predictive model.

It is possible to define a parameter category as "SNP related to PCa biomarker concentration" or "SNP related to PCa biomarker expression level" which includes SNP related to the concentration or expression level of relevant biomarkers such as Prostate-specific antigen (PSA) in either free form or complexed form, pro PSA (a collection of isoforms of PSA) and in particular the truncated form (−2) pro PSA, intact PSA, human prostatic acid phosphatase (PAP), human kallikrein 2 (hK2), early prostate cancer antigen (EPCA), Prostate Secretory Protein (PSP94; also known as beta-microseminoprotein and MSMB), glutathione S-transferase π (GSTP1), α-methylacyl coenzyme A racemase (AMACR), and Macrophage Inhibitory Cytokine 1 (MIC-1; also known as GDF-15). A subset of the members of this category would be sufficient to represent the category as such in a predictive model.

Suitable SNPs related to other processes than PCa further include, but are not limited to rs3817334, rs10767664, rs2241423, rs7359397, rs7190603, rs571312, rs29941, rs2287019, rs2815752, rs713586, rs2867125, rs9816226, rs10938397, and rs1558902 all being related to the BMI of an individual. Other suitable SNP related to BMI are disclosed in the report "Contribution of 32 GWAS-identified common variants to severe obesity in European adults referred for bariatric surgery" by Magi and co-authors as published in PLoS One. 2013 Aug. 7; 8(8):e70735 (which is incorporated by reference herein). It is possible to define a parameter category as "SNP related to expression level of BMI" which includes SNP related to the BMI of the individual. A subset of the members of this category would be sufficient to represent the category as such in a predictive model.

A preferred collection of SNP to be used in the assessment of the presence or non-presence of aggressive prostate cancer in a subject is rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573. Even though the use of the complete list is preferable, any subset of this list is suitable for use in the assessment of the presence or non-presence of aggressive prostate cancer in a subject. The SNP in this list (all, or a subset comprising about 95%, or 90%, or 85%, or 80%, or 75%, or 70%, of the SNP in this list) may be placed on the same solid support, for example the same glass slide, for simultaneous detection in a suitable analytical instrument.

As has been discussed previously, the assessment of the performance of PCa screening efficiency is difficult. Although the ROC-AUC characteristics provide some insight regarding performance, additional methods are desirable. One alternative method for assessing performance of PCa screening is to calculate the percentage of positive biopsies at a given sensitivity level and compare the performance of screening using PSA alone with any novel method for screening. This however requires that the performance of PSA is accurately defined.

One example of an assessment performance of PSA screening has been disclosed by IM Thompson and co-authors in the report "Assessing prostate cancer risk: results from the Prostate Cancer Prevention Trial." as published in J Natl Cancer Inst. 2006 Apr. 19; 98(8):529-34 (which is incorporated by reference herein). In this report, prostate biopsy data from men who participated in the Prostate Cancer Prevention Trial (PCPT) was used to determine the sensitivity of PSA. In total, 5519 men from the placebo group of the PCPT who underwent prostate biopsy, had at least one PSA measurement and a digital rectal examination (DRE) performed during the year before the biopsy, and had at least two PSA measurements performed during the 3 years before the prostate biopsy was included. This report discloses that when using a PSA value of 3 ng/mL as a cutoff about 41% of the high-grade cancers (i.e. cancers with Gleason score 7 or above) will be missed.

A second analysis using the same study population has been disclosed by IM Thompson and co-authors in "Operating characteristics of prostate-specific antigen in men with an initial PSA level of 3.0 ng/ml or lower" as published in JAMA. 2005 Jul. 6; 294(1):66-70 (which is incorporated by reference herein). In this report, the authors present an estimate of the sensitivity and specificity of PSA for all prostate cancer, Gleason 7+ and Gleason 8+. When using 3.1 ng/mL as PSA cut off value for biopsy a sensitivity of 56.7% and a specificity of 82.3% for Gleason 7+ tumors was estimated. In this report the authors concluded that there is no cut point of PSA with simultaneous high sensitivity and high specificity for monitoring healthy men for prostate cancer, but rather a continuum of prostate cancer risk at all values of PSA. This illustrates the complication with PSA as a screening test while still acknowledging the connection of PSA with prostate cancer.

One inevitable consequence of the difficulties in obtaining accurate and comparable estimates of the predictive performance of any given diagnostic or prognostic model in the screening of PCa is that when calculating the relative improvement of a novel method as compared to using PSA alone, the calculated relative improvement will vary depending on many factors. One important factor that influences the calculated relative improvement is how the control group (i.e. known negatives) is obtained. Since it is unethical to conduct biopsies on subjects where there are no indications of PCa, the control group will be selected with bias. Thus, the relative improvement of a novel method will depend on how the control group was selected, and there are multiple fair known methods to select control groups. Any reported estimated improvement must therefore be seen in the light of such variance. To the best of our experience, we estimate that if the relative improvement of a novel method is reported to be 15% as compared to the PSA value alone using one fair known method for selecting the control group, said novel method would be at least 10% better than the PSA value alone using any other fair known method for selecting the control group.

To become used in a widespread manner in society, the performance of a screen must meet reasonable health economic advantages. A rough estimate is that a screening method performing about 15% better than PSA (i.e. avoiding 15% of the unnecessary biopsies) at the same sensitivity level, i.e. detecting the same number of prostate cancers in the population, would have a chance of being used in a widespread manner in the current cost level of public health systems. However, for defined subpopulations of individuals a novel screening method may have economic advantages also for smaller improvements as compared to the PSA value performance. It is noted that even though significant efforts have been put on finding a combined model for the estimation of PCa risk (as exemplified in several of the cited documents in this patent application), no such combined method is currently in regular use in Europe. Thus, previous known multiparametric methods do not meet the socioeconomic standards to be useful in modern health care. The method of the current invention has better performance than previously presented combined methods and meet the socioeconomic performance requirements to at all be considered by a health care system.

One possible method for obtaining a screening method for aPCa meeting the requirements for widespread use is to combine information from multiple sources. From an overview level, this comprises combining values obtained from biomarker analysis (e.g. PSA values), genetic profiles (e.g. the SNP profile), family history, and other sources. The combination as such has the possibility to produce a better diagnostic statement than any of the included factors alone. Attempts to combine values into a multiparametric model to produce better diagnostic statements have been disclosed in the past, as described elsewhere in the current application.

The combination of data can be any kind of algorithmic combination of results, such as a linear combination of data wherein the linear combination improves the diagnostic performance (for example as measured using ROC-AUC). Other possible methods for combining into a model capable of producing a diagnostic estimate include (but are not limited to) non-linear polynomials, support vector machines, neural network classifiers, discriminant analysis, random forest, gradient boosting, partial least squares, ridge regression, lasso, elastic nets, k-nearest neighbors. Furthermore, the book "The Elements of Statistical Learning: Data Mining, Inference, and Prediction, Second Edition" by T Hastie, R Tibshirani and J Friedman as published by Springer Series in Statistics, ISBN 978-0387848570 (which is incorporated by reference herein) describes many suitable methods for combining data in order to predict or classify a particular outcome.

The algorithm which turns the data from the different categories into a single value being indicative of if the patient is likely to suffer from aPCa is preferably a non-linear function, wherein the dependency of different categories is employed for further increasing the diagnostic performance of the method. For example, one important dependency is the measured level of a selected biomarker combined with any associated genetic marker related to the expected expression level of said biomarker. In cases where an elevated concentration of the biomarker is found in a patient sample, and at the same time said patient is genetically predisposed of having lower levels of said biomarkers, the importance of the elevated biomarker level is increased. Likewise, if a biomarker level is clearly lower than normal in a patient being genetically predisposed to have high levels of said biomarkers, the contradictory finding increases the importance of the biomarker level interpretation. The algorithm used for predicting the risk for aggressive PCa may benefit from using transformed variables, for example by using the log 10(PSA) value. Transformation is particularly beneficial for variables with a distribution that is deviating clearly from the normal distribution. Possible variable transformations include, but are not limited to, logarithm, inverse, square, and square root. It is further common to center each variable to zero average and unit variance.

Although the combining of data can be performed in different ways, a typical procedure according to the present invention can be illustrated in the following non-limiting manner.

In a typical case, data regarding biomarkers belonging to a parameter category will be combined according to a predetermined equation to form a composite value which is related to the risk related to the parameter category as such. One non-limiting example is to calculate the average value of all available measurement values (data) for the members of a biomarker category, and use said average value as the composite value representing said biomarker category. This procedure may clearly be applied regardless of how many biomarker members belong to the category. If only data for one of the biomarkers included in a category is available, it can be used in itself to represent the biomarker category. For biomarkers, the measured value commonly used in the step of combination of data is the concentration of said biomarker found in the biological sample. For example, for the biomarkers PSA and HK2, this is most commonly the concentration of biomarker in a blood sample as expressed in units ng/mL.

The genetic score (i.e. the genetics composite value, or more specifically the SNP composite value) calculation is typically based on a predetermined odds ratio for each individual SNP included in a parameter category. For each SNP the odds ratio, i.e. the likelihood that an individual who carries a SNP (i.e. has the risk allele defined by the SNP) has the disease or condition under study, is determined in advance. Determination of the odds ratio for a SNP is usually done in large prospective studies involving thousands of subjects with known conditions or diseases.

The genetic score for an individual can, as a non-limiting example, be computed according to the following algorithm: For the individual at test, each SNP is processed in the following manner. For each SNP the individual may carry two SNP risk alleles (homozygous positive for said SNP), or one risk allele (heterozygous positive for said SNP) or zero risk alleles (homozygous negative for said SNP). The number of alleles for a SNP is multiplied with the natural logarithm of the odds ratio for said SNP to form a risk assessment value for that particular SNP. This means that an individual who is negative for a particular SNP (i.e. has zero SNP risk alleles) will have no risk contribution from said particular SNP. This procedure is repeated for all SNP for which measurement data is available. When all risk assessment values have been calculated, the average of the risk contribution for the SNP for which measurement data are available is calculated and is used as the genetic score for said individual, i.e. the genetics composite value with respect to a certain category of SNPs. This procedure may clearly be applied regardless of how many SNP members belong to the SNP category.

To further illustrate a typical procedure according to the present invention, when applied to an individual, the following assumptions are made. Two parameter categories are defined, firstly a protein biomarker category (or biomarker category) having the members Prot1 and Prot2, and secondly a genetic category (or more specifically, a SNP category) having the members Snp1, Snp2, and Snp3. In an experiment involving 100 individuals with the known condition C and 100 individuals known not to have condition C, the relationship of Prot1, Prot2, Snp1, Snp2, and Snp3 with the condition C is established and formulated as one protein biomarker composite value for Prot1 and Prot2, and one genetic composite value for Snp1, Snp2, and Snp3, and also one overall composite value which in turn is related to the risk of having condition C. The composite value for the protein biomarker category is calculated using the following predetermined equations:

$P=(Prot1+2*Prot2)/3$ [if data regarding both Prot1 and Prot2 (i.e. both Prot1 value and Prot2 value) are available]

$P'=Prot1$ [in case only data regarding Prot1 (i.e. the Prot1 value) is available]

$P''=Prot2$ [in case only data regarding Prot2 (i.e. the Prot2 value) is available]

Hence, in this hypothetical case it was found in the experiment that (a) Prot1 and Prot2 has the same scale and (b) the value of Prot2 is twice as important for assessing if an individual has condition C than Prot 1. If only data for one of the protein biomarkers is available it can be used in itself to represent the protein biomarker category. The odds ratios for the members of the genetic category had been determined in advance and were the following: Snp1=1.1; Snp2=1.2; and Snp3=1.3. The composite value for the genetic category is calculated as the genetic score described above. The protein biomarker composite value and the genetic score (which in this case is equivalent to the genetic category composite value, or the SNP composite value) are then combined into an overall composite value according to the following predetermined equation:

$$Y=P+10*score$$

where Y is related to the risk of having condition C, P is the protein biomarker composite value (and P may be substituted by P' or P'' as defined above), and score is the genetic score. All equations need to be developed based on a large group of individuals, in this hypothetical case the 100+100 individuals, in which the relationship between Y and the disease or condition under study is derived. In this hypothetical case it is assumed that if Y>5 the risk for the individual to have condition C is elevated and if Y>10 the risk is very high.

Now assume that a first individual A is being tested for Prot1, Prot2, Snp1, Snp2, and Snp3. In this particular case, all measurements were successful and produced the following results:
Prot1=3 ng/mL
Prot2=6 ng/mL
Snp1=homozygous negative i.e. no risk alleles=0
Snp2=heterozygous positive, i.e. one risk allele=1
Snp3=homozygous positive, i.e. two risk alleles=2

The composite value for the protein biomarker category will in this case be P=(3+2*6)/3=5. The composite value for the genetic category, also known as the genetic score, becomes score=(0*log(1.1)+1*log(1.2)+2*log(1.3))/3=0.2357. The overall composite value becomes Y=5+10*0.2357=7.357. Hence, the risk of having condition C for the individual A is estimated to be elevated but not very high.

Now further assume that a second individual B is being tested for Prot1, Prot2, Snp1, Snp2, and Snp3. In this particular case, three measurements were successful and produced the following results:
Prot1=2 ng/mL
Prot2=MISSING DATA
Snp1=homozygous positive, i.e. two risk alleles=2
Snp2=MISSING DATA
Snp3=heterozygous positive, i.e. one risk allele=1

The composite value for the protein biomarker category will in this case be P'=2, because only Prot1 results are available. The composite value for the genetic category, also known as the genetic score, becomes score=(2*log(1.1)+1*log(1.3))/2=0.2264. The overall composite value becomes Y=2+10*0.2264=4.264. Hence, the risk for the individual B of having condition C is estimated to be low.

Generally, in models predicting the risk for developing aPCa, there is often one or more cut-off values defined. The choice of cut-off value (or cut-off level) depends on many factors, including but not limited to the risk of the disease as such and the risk associated with inaccurately diagnosing an individual as positive who do not have the disease (false positive). In the general case, a predictive model is usually a monotonic function Y=f(x1, x2, . . . , xN) where the estimated risk of having the disease is correlated with the increasing value of Y. This means that if the cut-off value is set at a low level, the test will produce a large number of false positive results, but will on the other hand detect most individuals that actually have the disease. If the cut-off level is set at a high value the opposite occurs where individuals having a Y value above the cut-off level will with very high probability have the disease, but a large number of individuals with disease will receive a negative test results (i.e. large number of false negative results). The choice of cut-off level depends on many factors, including the socio-economic outcome of balancing (a) missing individuals with the disease and (b) treating individuals without the disease.

When applied in practice, it will occasionally happen that one or a few measurements fail due to for example unforeseen technical problems, human error, or any other unexpected and uncommon reason. In such cases the data set obtained for an individual will be incomplete. Typically, such an incomplete data set would be difficult or even impossible to evaluate. However, the current invention relies on measurements of a large number of features of which many are partially redundant. This means that also for individuals for which the data set is incomplete, it will in many cases be possible to produce a high-quality assessment according to the invention. This is particularly true within categories, where for example the kallikrein-like biomarkers are correlated and partially redundant. Technically, it is therefore possible to apply an algorithmic two-step approach, wherein the kallikrein biomarker contribution is summarized into a kallikrein score (or kallikrein value). This kallikrein score is then in a second step being combined with other data (such as genetic score, age, and family history to mention a few non-limiting examples) to produce a diagnostic or prognostic statement on PCa. Similar two-step procedures can be implemented for other classes of markers, such as genetic markers related to BMI or protein biomarkers related to transforming growth factor beta superfamily (a large family of structurally related cell regulatory proteins that includes MIC-1), to mention two non-limiting examples.

The redundancy aspect can be embodied in many different manners. One possible way to implement the redundancy aspect is to define a set of biomarkers representing biomarkers related to a common field or family. One non-limiting example of such a field or family is kallikrein-like biomarkers. More than one defined set (or category) of biomarkers can be determined, and in addition still other biomarkers can be applied outside such a set. Typically, the categories are non-overlapping, i.e. any defined biomarker is only member of one defined category or used in a solitary manner Next, for all biomarkers an attempt to determine a presence or concentration is made. In most cases the determination for all biomarkers will succeed, but occasionally one or a few values will be missing. To induce model robustness to missing values, it is possible to define a biomarker category composite value which can be determined using all or a subset of the members of the defined category. To work in practice, this requires that the members of the defined category of biomarkers are at least partially redundant. In the next step, the biomarker category composite value is combined with other biomarker values, other biomarker category composite values (if two or more categories of biomarkers were defined), genetic score related to PCa risk, genetic score related to other features (such as BMI or biomarker concentration, to mention two non-limiting examples), family history, age, and other information carriers related to aPCa risk into an overall composite value. The overall composite value is finally used for the estimation of aPCa risk.

The purpose of the biomarker category composite value is hence to serve as an intermediate value which can be estimated using incomplete data. Assume that a defined category of biomarker comprises N different biomarkers denoted B1, B2, B3, . . . BN, all related to the biomarker family B. In that case, there could be N different models available for calculating the family B biomarker composite value C:

$$C = f1(B1, B2, B3, \ldots BN)$$
$$C = f2(B2, B3, \ldots BN)$$
$$C = f3(B1, B3, \ldots BN)$$
$$\ldots$$
$$C = fN(B1, B2, B3, \ldots BN-1)$$

Wherein f1( ), f2( ) . . . fN( ) are mathematical functions using the values for biomarkers B1, . . . BN as input and in some manner producing a single output C representing family B biomarker composite value. One non-limiting example of the functions f1( ), . . . fN( ) include linear combinations of the present arguments. With such a set of multiple functions capable of calculating C for all the cases of one single biomarker value missing, the calculation of the overall composite value becomes less sensitive to missing data. It is understood that the estimate of C might be of less good quality when not all data is present, but may still be good enough for use in the assessment of PCa risk. Thus, using such a strategy, only N-1 biomarker determinations have to succeed in order to produce an estimate of C. It is further possible to develop estimates for any number of lost data, i.e. if N-2 biomarker determinations have to succeed, another set of functions f( ) could be developed and applied to estimate C.

Thus, with respect to PCa biomarkers, the present invention relates to a method that is based on a redundantly designed combination of data, as defined elsewhere in the present application. More specifically, the method comprises measuring the presence or concentration of at least partially redundant PCa biomarkers, and wherein at least one, such as two, of the PCa biomarkers is selected from the group consisting of (i) PSA, (ii) total PSA (tPSA), (iii) intact PSA (iPSA), (iv) free PSA (fPSA), and (v) hK2. The method allows disregarding a subset of at least one of the PCa biomarkers (i)-(v) when forming the biomarker composite value. In other words, the method allows that the biomarker composite value is formed from data regarding less than all PCa biomarkers of the biomarker category, more specifically data regarding a subset of at most four of said PCa biomarkers. As the skilled person will appreciate, this will be equivalent to a method where data regarding a subset of at most four of said PCa biomarkers are required to form said biomarker composite value. It is an advantage of the method according to the present invention that omission, lack, or loss of data regarding a subset of said PCa biomarkers is acceptable when forming the biomarker composite value.

As the skilled person will appreciate, the present invention includes that the method comprises forming the biomarker composite value from data regarding all biomarkers of the biomarker category, provided that data regarding all biomarkers are available.

In an embodiment, the method allows disregarding a subset of one, two, three, or four of the PCa biomarkers (i) PSA, (ii) total PSA (tPSA), (iii) intact PSA (iPSA), (iv) free PSA (fPSA), and (v) hK2. In other words, the method allows that said biomarker composite value is formed from data regarding a subset of four, three, two or one of the PCa biomarkers (i)-(v), respectively.

As mentioned earlier in the present application, the method may further comprise analyzing one or each of a plurality of additional categories of PCa biomarkers, wherein the combination of data to form each additional biomarker composite value is redundantly designed where the additional category of PCa biomarkers comprises more than one PCa biomarker. The method allows disregarding a subset of the PCa biomarkers when forming the biomarker composite value. In other words, the method allows that the biomarker composite value is formed from data regarding less than all PCa biomarkers of the additional biomarker category, such as data regarding a subset of 10%, 20%, 30%, 40%, 50%, 60%, 70%, 80%, or 90% of the PCa biomarkers of the additional PCa biomarker category. As the skilled person will appreciate, the present invention includes that the method comprises forming each additional biomarker composite value from data regarding all PCa biomarkers of the PCa biomarker category, provided that data regarding all PCa biomarkers are available.

Genetic risk scores (i.e. genetic scores, or genetics composite values, more particularly SNP composite values) are also insensitive to small losses of data due to for example unforeseen technical problems, human error, or any other unexpected and uncommon reason. The contribution of one snp to the risk score is typically not correlated to any other snp. In the case of snp, the risk change due to each snp is small, but by using multiple snp related to a condition in concert, the risk change for said condition becomes large enough for having an impact on the model performance. The preferred number of snp to form a genetic score is at least 3 snp, preferably 10 snp, more preferably 25 snp, still more preferably 50 snp, more preferably, 60 snp, still more preferably 70 snp, yet more preferably 80 snp, more preferably 90 snp, yet more preferably 100 snp, still more preferably 150 snp, yet more preferably 200 snp, still more preferably 250, and still even more preferably 300 snp. This means that the impact of any single snp on the total result is typically small, and the omission of a few snp will typically not alter the overall genetic score risk assessment in any large manner, i.e. will typically not alter the SNP composite value to a significant extent. In current state of the art, the typical data loss in the large scale genetic measurements is on the order of 1-2%, meaning that if a genetic score is composed of 100 different snp, the typical genetic characterization of an individual would provide information about 98-99 of these snp's. The present model as such, as discovered in the work of the present invention, can however withstand a larger loss or lack of data, such as 5-7% loss of information, or 7-15%, or even 15-30%. In this sense, the combination of data regarding SNPpc is at least partially redundant.

Consequently, also with respect to genetic markers (SNPs), the present invention relates to a method that is based on a redundantly designed combination of data, as defined elsewhere in the present application. The method allows disregarding at least 5% of the SNPpc when forming the SNP composite value. In other words, the method allows that said SNPpc composite value is formed from data regarding less than all SNPpc of the SNPpc category, more specifically data regarding a subset of at most 95% of said SNPpc. As the skilled person will appreciate, this will be equivalent to a method where data regarding a subset of at most 95% of said SNPpc are required to form said SNPpc composite value. It is an advantage of the method according to the present invention that omission, lack, or loss of data regarding a subset of said SNPpc is acceptable when forming the SNPpc composite value.

As the skilled person will appreciate, the present invention includes that the method comprises forming the SNPpc composite value from data regarding all SNPpc of the SNPpc category, if data regarding all SNPpc are available. Similarly, the present invention includes that the method comprises forming the SNPpc composite value from data regarding a subset of 99%, 98%, 97%, or 96% of said SNPpc.

In an embodiment, the method allows disregarding 6%, 7%, 8%, 9%, 10%, 15%, 20%, 25%, or 30% of the SNPpc when forming the SNPpc composite value. In other words, the method allows that said SNPpc composite value is formed from data regarding a subset of 94%, 93%, 92%, 91%, 90%, 85%, 80%, 75%, or 70% of the SNPpc, respectively.

One non-limiting example of such a redundantly designed combination of data is a calculation of the average of the risk related to each SNP for which measurement data exist. Another non-limiting example of such a redundantly designed combination of data is to provide multiple independent equations to calculate the composite value, one equation for each subset of data that can be used to produce said composite value.

One suitable method for associating a SNP with a condition (for example PCa, or BMI>25, or elevated hk2 biomarker concentration in blood) has been described in the public report "Blood Biomarker Levels to Aid Discovery of Cancer-Related Single-Nucleotide Polymorphisms: Kallikreins and Prostate Cancer" by Robert Klein and co-authors as published in Cancer Prev Res 2010; 3:611-619 (which is incorporated by reference herein). In this report, the authors describe how they could associate the SNP rs2735839 to elevated value of (free PSA)/(total PSA). Furthermore, they could associate the SNP rs10993994 to elevated PCa risk, elevated total PSA value, elevated free PSA value and elevated hk2 value, and finally SNP rs198977 was associated with elevated PCa risk, elevated value of (free PSA)/(total PSA), and elevated hk2 value.

In practice, one common method for associating a SNP with a condition relies on access to a case-control clinical trial which compares two large groups of individuals, one healthy control group and one case group having the condition under study. All the individuals in each group are genotyped for the majority of common known SNPs. When all genotyping data is available, it is investigated if the allele frequency is significantly altered between the case group and the control group. In such setups, the typical unit for reporting effect sizes is the odds ratio. The odds ratio reports the ratio between two proportions: the proportion of individuals in the case group having a specific allele, and the proportions of individuals in the control group having the same allele. If the allele frequency in the case group is significantly higher than the allele frequency in the control group, the odds ratio will be higher than 1. If the allele frequency in the case group is significantly lower than the allele frequency in the control group, the odds ratio will be smaller than 1.

One preferred method for combining information from multiple sources has been described in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein). Associations between each SNP and PCa at biopsy were assessed using a Cochran-Armitage trend test. Allelic odds ratios (OR) with 95% confidence intervals were computed using logistic regression models. For each patient, a genetic risk score was created by summing up the number of risk alleles (0, 1, or 2) at each of the SNPs multiplied by the logarithm of that SNP's OR. Associations between PCa diagnosis and evaluated risk factors were explored in logistic regression analysis. The portion of the model related to non-genetic information included logarithmically transformed total PSA, the logarithmically transformed free-to-total PSA ratio, age at biopsy, and family history of PCa (yes or no). A repeated 10-fold cross-validation was used to estimate the predicted probabilities of PCa at biopsy. Ninety-five percent confidence intervals for the ROC-AUC values were constructed using a normal approximation. All reported p values are based on two-sided hypotheses.

There are many rational reasons for distinguishing between prostate cancer in general and aggressive prostate cancer. In most cases, prostate cancer is a slowly progressing disease. The fact that most men are diagnosed late in life means that a large fraction of the men diagnosed with prostate cancer die of other causes. Thus, the ability to estimate if an individual is at elevated risk for having aggressive prostate cancer, prior to biopsy, makes it possible for example to motivate the individual to change life-style. To stop smoking, to reach a BMI value below 30 and to exercise regularly (approximately 30 minutes 3-6 days of the week) are all factors that in general promotes survival in conditions of severe disease, including prostate cancer. Hence, if an individual is found having elevated risk for aPCa it is reason to suggest to said individual to stop smoking, try to reach BMI<30 and start exercising. Another important aspect is dietary issues. Through changing the diet, the PCa development may be reduced or delayed. There is evidence suggesting that reduced dairy intake can reduce the risk for onset of PCa as reported by Song and co-authors in the publication "Whole milk intake is associated with prostate cancer-specific mortality among U.S. male physicians." as published in J Nutr. 2013 February;143(2):189-96 (which is incorporated by reference herein). Similar evidence exists for the positive effects of intake of green tea and intake of soy products. Hence, if an individual is found having elevated risk for aPCa it is reason to suggest to said individual to decrease intake of dairy products and/or increase intake of green tea and soy based products.

Example 1

To illustrate the current invention, a data set comprising 215 cases (subjects known to suffer from aPCa with a Gleason grade of 7 or higher) and 627 controls (subjects known not to suffer from aPCa) from the STHLM2 data set was extracted. The STHLM2 data set has been discussed in the public domain as evident on the web-page http://sthlm2.se/. In summary, during 2010-2012 about 26000 men who did a PSA test in the Stockholm area were included in the STHLM2 study. The 215+627=842 subjects were characterized with respect to the following biomarkers and SNPs.

Biomarkers:
Total prostate-specific antigen (tPSA) [ng/mL]
Intact prostate-specific antigen (iPSA) [ng/mL]
Free prostate-specific antigen (fPSA) [ng/mL]
human kallikrein 2 (hK2) [ng/mL]
Macrophage Inhibitory Cytokine 1 (MIC-1) [ng/mL]
beta-microseminoprotein (MSMB) [ng/mL]

SNPs:
657de15, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, rs9623117

Background information for each subject was collected, including age and family history (yes or no). Age was expressed in the units of years.

In order to decide which subjects that should be referred to biopsy, it is required to predict a value for each tested subject that is correlated with the probability that said subject has prostate cancer with a Gleason grade of 7 or higher. This can be done by combining measured values of the biomarkers in the following predetermined equation:

$$y=-0.4366579+0.0577639*\text{score}-0.1026622*\text{HK2}-0.0312050*\text{fPSA}+0.0640730*\text{iPSA}+0.0256631*\text{MIC1}-0.0069049*\text{MSMB}+0.0012231*\text{tPSA}+0.0069759*\text{age}$$

In this equation, 'score' is here the genetic score variable computed as described in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein), containing the validated prostate cancer susceptibility SNPs (said SNP being related to prostate cancer susceptibility or related to PSA, free-PSA, MSMB and MIC-1 biomarker plasma levels) listed in the present example. The parameters 'HK2', 'fPSA', 'iPSA', 'MIC1', 'MSMB', 'tPSA' refer to the respective measured values (untransformed) of these biomarkers and 'age' is the age of the subject. The equation was derived using the ordinary least squares estimator (other linear estimators can also straight-forwardly be used, e.g. the logistic regression estimator). In this particular model, information regarding family history was omitted.

The resulting value 'y' will be strongly correlated with the risk of having prostate cancer with a Gleason grade of 7 or higher, as illustrated in FIG. 1. The ROC curves in FIG. 1 represent PSA (101) alone and the model described in this example (102). If y is above a cutoff value the man should be recommended a referral to a urologist for examination of the prostate using biopsies. The fact that this model predicts aggressive, high-grade PCa implicitly means that if the resulting value 'y' is small, there is still a risk for the patient having PCa albeit a non-aggressive form. A small resulting value 'y' may also indicate that the patient has no PCa.

The value of the cutoff depends on the tradeoff between test sensitivity and specificity. If, for example, the cut off value of 0.166 is used, this particular test will result in test sensitivity of 0.9 and specificity of 0.38. This can be compared to using the PSA value alone as a screening test, which results in a sensitivity of 0.9 and specificity of 0.22. In practice, this means that this particular model as applied to the population of 827 subjects would result in the same number of detected high risk cancers (Gleason grade 7 and above) as the PSA test, but with 100 subjects less being referred to biopsy, which corresponds to an improvement of approximately 15% compared to the PSA test alone. If, as a second example, the cut off value of 0.201 is used, this particular test will result in test sensitivity of 0.8 and specificity of 0.52. At the sensitivity level 0.8, approximately 20% of the biopsies as predicted using PSA would be saved.

Example 2

Figure 2:
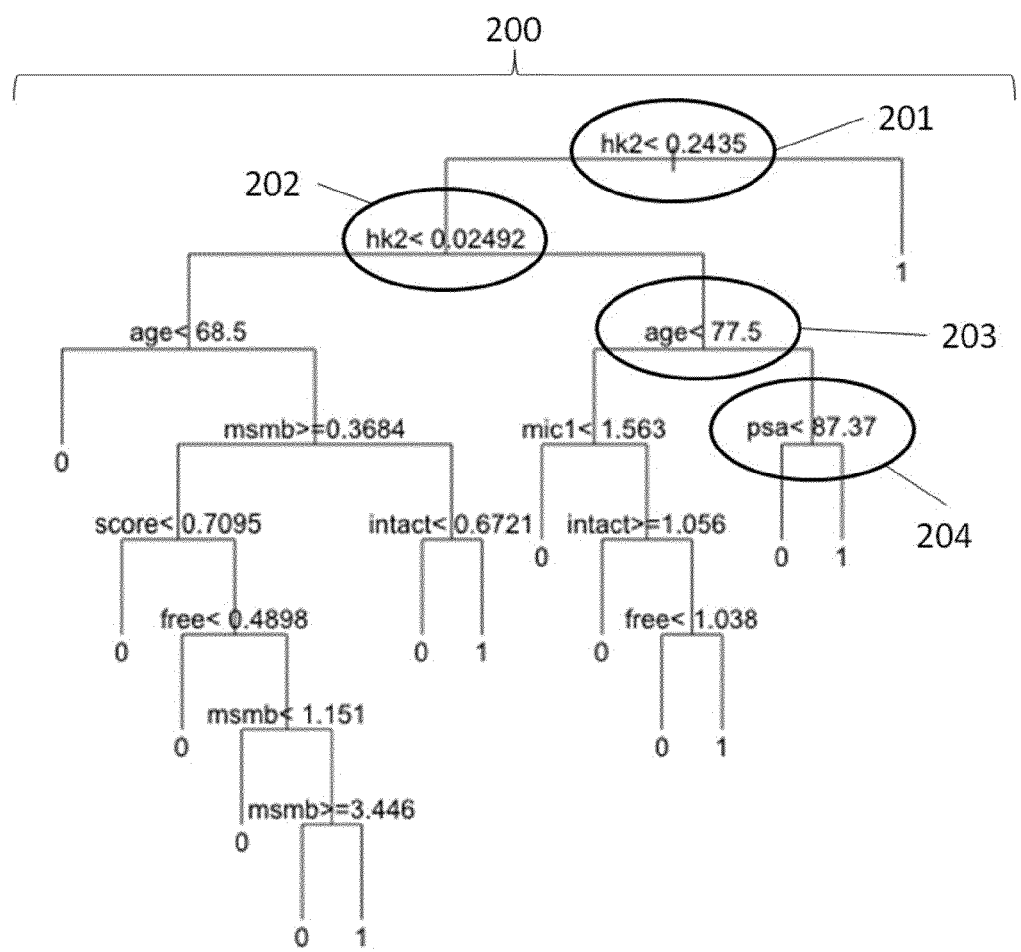
FIG. 2 shows an example of a decision tree to predict whether a subject should be referred to biopsy.

To illustrate the current invention further, an alternative computational method for obtaining a prediction was applied. Equations such as the one presented in Example 1 are not the only way in which the biomarkers can be combined to predict aPCa. In fact, the method for calculating y in order to predict aPCa can be intricate and not even possible to write down in on a sheet of paper. A more complicated but very powerful example of how the biomarkers can be combined is to use a forest of decision trees. An example of a decision tree (200) is depicted in FIG. 2. Suppose that an 81 year old subject tested for biomarkers and SNPs with results HK2=0.2425 and PSA=84.1. When applying the decision tree (200) as exemplified in FIG. 2 the top node (201) is related to the hk2 value. Since the subject has a HK2 value, which does satisfy the node condition, one follows the left branch from that node. The second node (202) is also related to the hk2 value, and in this case the subject has an hk2 value which does not satisfy the node condition, and then one follows the right branch from that node. The third level node (203) is related to age. Since the subject age does not satisfy the node condition, one follows the right branch from that node. The fourth level node (204) is related to the PSA value, and since the PSA value of the subject does satisfy the node condition, one follows the left branch from that node. At this point, there are no more nodes meaning that one has reached a leaf of the decision tree. Each leaf has a corresponding output, in this particular example a leaf value of "1" means "do refer to biopsy" and "0" means "do not refer to biopsy". The exemplary subject did in this case end up in a leaf with value "0", meaning that the prediction provided by this decision tree is "do not refer to biopsy".

A problem with relying on merely one decision tree for calculating y to predict aPCa is that a single decision tree has very high variance (i.e. if the data changed slightly the calculated value of y is also likely to change, leading to variance in the prediction of aPCa), although its bias is very low. One possible method for reducing the high variance it to construct a forest of decorrelated trees using the random forest algorithm as described in the report "Random Forests" by Leo Breiman as published in Machine Learning 45 (1): 5-32 (2001) (which is incorporated by reference herein). A large number of trees are grown, and before the growth of each tree the data is randomly perturbed in such a way that the expected value of its prediction is unchanged. To predict aPCa, all trees cast a vote to decide whether a subject should be referred to biopsy. Such a voting prediction retains the unbiased properties of decision trees, however considerably lowers the variance (similarly to how the variance of a mean is lower than the variance of the individual measurements used to compute the mean). Since the random forest algorithm depends on random number generation, it is a complex procedure to write down the resulting prediction algorithm in closed form.

When applied to the data set as described in Example 1, this model can at sensitivity 0.9 save approximately 20% of the number of biopsies compared to PSA alone.

Example 3

To illustrate the current invention even further, a data set comprising 51 cases (subjects known to suffer from aPCa with a Gleason grade of 7 or higher) and 195 controls (subjects known not to suffer from aPCa) from the STHLM2 data set was extracted. All these cases and controls had a BMI value greater than 25. The 51+195=246 subjects were characterized with respect to the following biomarkers.
Biomarkers:
Total prostate-specific antigen (tPSA) [ng/mL]
Intact prostate-specific antigen (iPSA) [ng/mL]
Free prostate-specific antigen (fPSA) [ng/mL]
human kallikrein 2 (hK2) [ng/mL]
Macrophage Inhibitory Cytokine 1 (MIC-1) [ng/mL]
beta-microseminoprotein (MSMB) [ng/mL]

The same SNPs as defined in the previous example 1 were applied also in this example. Background information for each subject was collected, including if the subject had undergone a previous biopsy (prevBiop) of the prostate, age and family history (yes or no). Age was expressed in the units of years, height in meters and weight in kilograms.

In order to decide which subjects that should be referred to biopsy, it is required to predict a value for each tested subject that is correlated with the probability that said subject has prostate cancer with a Gleason grade of 7 or higher. This can be done by combining measured values of the biomarkers into an overall composite value using the following predetermined equation:

$$y=21.487704+0.548938*\text{prevBiop}+0.014242*\text{GenScore}+0.311481*\text{hk2}-0.043471*\text{fPSA}+0.047176*\text{iPSA}+0.068407*\text{mic1}-0.008860*\text{msmb}+0.002693*\text{tPSA}+0.006325*\text{age}-0.121356*\text{height}+0.119005*\text{weight}-0.388930*\text{bmi}$$

In this equation, 'score' is here the genetic score variable computed as described in the previous example 1. The parameters 'HK2', 'fPSA', 'iPSA', 'MIC1', 'MSMB', 'tPSA' refers to the respective measured values (untransformed) of these biomarkers and 'age', 'height', 'weight', and 'bmi' are the age, height, weight, and bmi of the subject. The parameter 'prevBiops' denotes if the subject has previously undergone prostate biopsy, reflecting a medical history of said subject. The equation was derived using the ordinary least squares estimator (other linear estimators can also straight-forwardly be used, e.g. the logistic regression estimator). In this particular model, information regarding family history was omitted.

Figure 3:
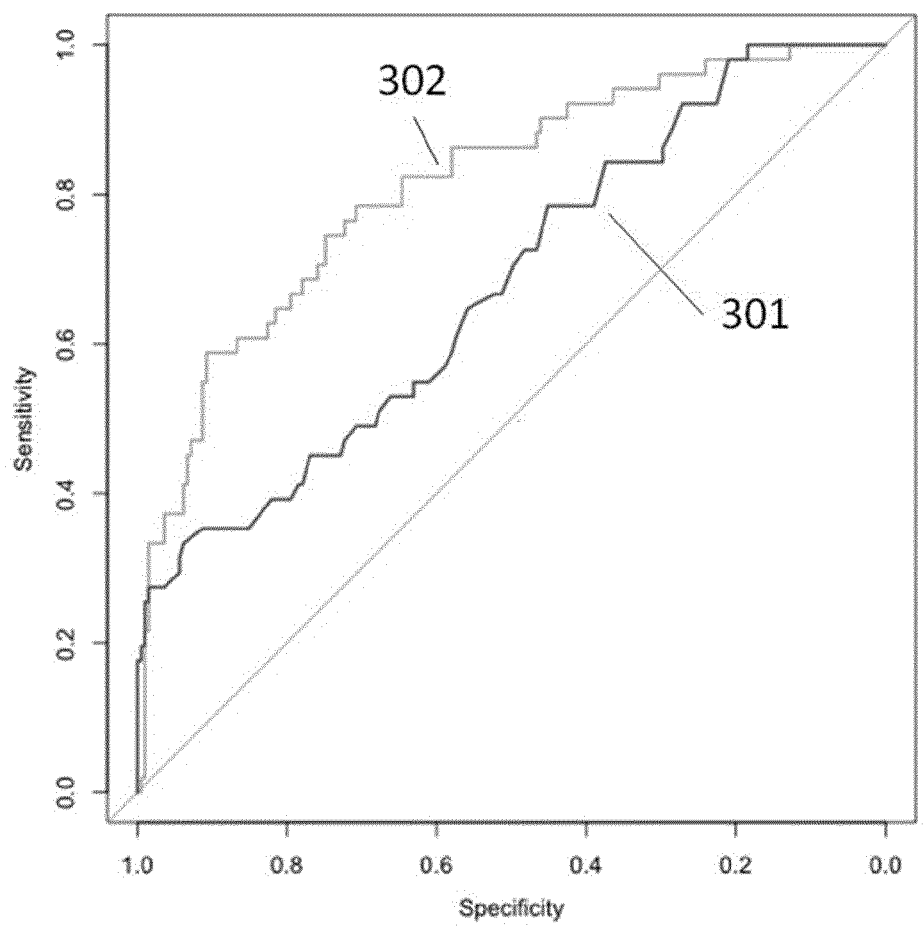
FIG. 3 shows the ROC curves for the linear model of Example 1 illustrating the difference in performance between PSA (301) and a multiparametric model (302) in prediction of aPCa for individuals with BMI value greater than 25.

The resulting value 'y' will be strongly correlated with the risk of having aggressive prostate cancer with a Gleason grade 7 or higher, as illustrated in FIG. 3. The ROC curves in FIG. 3 represent PSA (301) alone and the model described in this example (302). If y is above a cutoff value the man should be recommended a referral to an urologist for examination of the prostate using biopsies.

The value of the cutoff depends on the tradeoff between test sensitivity and specificity. If, for example, the cut off value of 0.201 is used, this particular test will result in test sensitivity of 0.8 and the test will save approximately 44% of the biopsies as compared to using PSA alone.

Example 4

To illustrate the aspects of parameter categories and redundancy within category even further, the data set of example 1 was characterized with respect to the following:
Biomarkers:
Total prostate-specific antigen (tPSA) [ng/mL]
Intact prostate-specific antigen (iPSA) [ng/mL]
Free prostate-specific antigen (fPSA) [ng/mL]
human kallikrein 2 (HK2) [ng/mL]
Macrophage Inhibitory Cytokine 1 (MIC-1) [ng/mL]
beta-microseminoprotein (MSMB) [ng/mL]

SNPs; belonging to the category SNPs related to PCa (SNPpc):
657de15, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, rs9623117

Background information for each subject was collected, including age and if a previous biopsy had been conducted (yes or no). Age was expressed in the units of years.

The equation for the overall composite value, which is used as the predictive model, was designed according to the predetermined equation:

$$Y=-0.632820+0.118107*K+0.139045*\text{prevBiopsy}+0.051609*\text{score}+0.048033*\text{MIC1}-0.001368*\text{MSMB}+0.008002*\text{age}$$

Where score is the genetic score, i.e. the composite value obtained from SNPs related to PCa (i.e. SNPpc composite value), as described previously, and K is the composite value for the parameter category for kallikrein-like biomarkers, MIC1 is the concentration of MIC1, MSMB is the concentration of MSMB, age is the age of the individual, and PrevBiopsy is 1 if the individual previously had had a biopsy conducted (and 0 if not). Depending on the availability of kallikrein data for a particular individual, the composite value for the category kallikrein-like biomarkers K was calculated in different ways.

$$K=(0.6122516+0.0012714*\text{fPSA}+0.0001864*\text{PSA}+0.0200385*\text{iPSA}-0.0377976*\text{HK2}-1.3108243\text{f}/\text{tPSA})/0.1559314$$

$$K'=(0.3961801+0.0001864*\text{PSA}+0.0200385*\text{iPSA}-0.0377976*\text{HK2})/0.109478$$

$$K''=(0.3961967+0.0012714*\text{fPSA}+0.0200385*\text{iPSA}-0.0377976*\text{HK2})/0.1090876$$

$$K'''=(0.3987352+0.0200385*\text{iPSA}-0.0377976*\text{HK2})/0.1033296$$

$$K''''=(0.6548828+0.0012714*\text{fPSA}+0.0001864*\text{PSA}-1.3108243\text{f}/\text{tPSA})/0.1068742$$

In these equations, PSA is the concentration of PSA, fPSA is the concentration of free PSA, iPSA is the concentration of intact PSA, HK2 is the concentration of HK2, and f/tPSA is the quotient of free PSA and total PSA. K is the parameter value suitable for use when all said kallikrein data is available. The parameters K', K'', K''', and K'''' are approximations of K that are suitable for use in cases where one or several of the kallikrein data are missing.

When testing the model discussed above, the following results were obtained:

Full model, all data included: ROC-AUC=0.77
Using all SNP and the K' approximation: ROC-AUC=0.70
Using all SNP and the K'' approximation: ROC-AUC=0.70
Using all SNP and the K''' approximation: ROC-AUC=0.70
Using all SNP and the K'''' approximation: ROC-AUC=0.75
Using K'''' data and randomly leaving out 10% of the SNP data: ROC-AUC=0.74
Using K'''' data and randomly leaving out 30% of the SNP data: ROC-AUC=0.73

As a reference point, when using only PSA to predict the risk for aPCa, the ROC-AUC=0.65. Hence, the model in the current example is (a) better than the reference model when all data is used, but also (b) robust to loss of input data, thanks to redundancy within parameter categories. It is possible to leave out one or more measurement results (i.e. data) for kallikrein-like biomarkers, also in combination with 10% (or even 30%) loss of the SNP information, and still produce useful results that are better than the reference model where PSA had been used alone. In a practical setting, such a robust operation makes it possible to estimate the risk for an individual to have aPCa even in cases where some data are missing due to either failing technology, lack of sample material, human error, or any other reason. This has the potential to reduce costs for the health care provider because the number of retests would be decreased. It would also make the situation for the individual more convenient with a more rapid response and alleviating the need for the individual to travel to the health care provider to supply a further sample for retesting procedures.

Although the invention has been described with regard to its preferred embodiments, which constitutes the best mode currently known to the inventor, it should be understood that various changes and modifications as would be obvious to one having ordinary skill in this art may be made without departing from the scope of the invention as set forth in the claims appended hereto.

The invention claimed is:

1. A method for determining aggressive prostate cancer (PCa) markers in an individual, comprising the steps of:
(i) Providing at least one biological sample from said individual;
(ii) Contacting the biological sample with an assay device comprising a first category of ligands which bind specifically to at least three kallikrein family protein PCa biomarkers, the first category of ligands including a plurality of different ligands binding specifically to each of the at least three kallikrein family protein PCa biomarkers, wherein the at least three PCa biomarkers include at least one of PSA, intact PSA (iPSA), total PSA (tPSA), free PSA (fPSA), and hK2;
(iii) Contacting the biological sample with an assay device comprising a solid phase having immobilised thereon a second category of ligands which bind specifically to at least 80 SNPs related to PCa (SNPpc), the second category of ligands including a plurality of different ligands binding specifically to each of said SNPpc, wherein
(a) said at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573; or
  (b) wherein said at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117;
(iv) Measuring
  a. a presence or concentration of each of said PCa biomarkers binding the ligands in said first category; and
  b. a presence or absence of each of said SNPpc binding the ligands in said second category;
(v) Combining measurement data of the at least three PCa biomarkers binding ligands from said first category from step (iv)a according to a first predetermined equation to form a biomarker composite value, wherein the combination according to the first predetermined equation allows omission of measurement data of a subset of said PCa biomarkers when forming said biomarker composite value, wherein the subset comprises at least one, but not all, of said three kallikrein family protein PCa biomarkers;
(vi) Combining measurement data of the at least 80 SNPpc binding ligands from said second category from step (iv)b according to a second predetermined equation to form a SNPpc composite value, wherein the combination according to the second predetermined equation allows omission of measurement data of a subset of at least 10%, and up to 30%, of the SNPpc when forming the SNPpc composite value; and
(vii) Combining the biomarker composite value and the SNPpc composite value according to a third predetermined equation to form an overall composite value.

2. The method of claim 1, wherein the combination according to the second predetermined equation allows omission of measurement data of at least 15% of the SNPpc when forming the SNPpc composite value.

3. The method of claim 2, wherein the combination according to the second predetermined equation allows omission of measurement data of at least 20% of the SNPpc when forming the SNPpc composite value.

4. The method of claim 1, wherein the at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117.

5. The method of claim 1, wherein the at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573.

6. The method of claim 1, further comprising collecting family history regarding PCa, treatment history, and physical data from said individual; and wherein said family history, treatment history and/or physical data are combined with the biomarker composite value and the SNPpc composite value according to the third predetermined equation to form said overall composite value.

7. The method of claim 1, further comprising contacting the biological sample with an assay device comprising a third category of ligands which bind specifically to at least one additional PCa biomarker selected from MIC-1 and MSMB, the third category of ligands including a plurality of different ligands binding specifically to each of the additional PCa biomarkers; measuring the presence or concentration of each of said at least one additional PCa biomarker binding the ligands in said third category; combining measurement data regarding said at least one additional PCa biomarker according to a fourth predetermined equation to form an additional biomarker composite value for said at least one additional PCa biomarker; and combining said additional biomarker composite value with the biomarker composite value and the SNPpc composite value according to the third predetermined equation to form the overall composite value; wherein the combination of measurement data to form the additional biomarker composite value allows omission of measurement data of at least one of the members of the additional category of PCa biomarkers where the additional category of PCa biomarkers comprises more than one PCa biomarker.

8. The method of claim 1, wherein said biological sample is a blood sample.

9. The method of claim 1, wherein said individual has a BMI value greater than 25.

10. The method of claim 1, wherein said assay device comprising a solid phase is a microarray.

11. The method of claim 1, wherein the measuring step employs at least two categories of detection molecules, wherein:
the first category of said detection molecules is capable of detecting the at least three kallikrein family protein PCa biomarkers; and
the second category of said detection molecules is capable of detecting the at least 80 SNPpc, wherein said at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117.

12. The method of claim 1, wherein steps (v)-(vii) are executed in a computer comprising a processor and memory.

13. The method of claim 1, wherein step (v) is conducted with a computer programmed to calculate a biomarker composite value from the measurement data of step (iv)a; step (vi) is conducted with a computer programmed to calculate a SNPpc composite value from the measurement data of step (iv)b; and step (vii) is conducted with a computer programmed to calculate an overall composite value from the data of steps (v) and (vi).

14. The method of claim 1, wherein the measuring step employs at least two categories of detection molecules, wherein:
the first category of said detection molecules is capable of detecting the at least three kallikrein family protein PCa biomarkers; and
the second category of said detection molecules is capable of detecting the at least 80 SNPpc, wherein said at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs48331039, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573.

15. The method of claim 1, wherein combining the measurement data of said PCa biomarkers according to the first predetermined equation comprises calculating a weighted average value of the measurement data of said PCa biomarkers based on the importance of the respective PCa biomarkers in a determination of aggressive PCa.

16. The method of claim 1, wherein combining the measurement data of said SNPpc according to the second predetermined equation comprises calculating an average value of an odds ratio of each individual SNPpc included in said category of SNPpc, wherein the odds ratio of an individual SNPpc is based on the likelihood that an individual who carries the individual SNPpc has aggressive PCa.

17. The method of claim 1, wherein the third predetermined equation comprises a linear equation or a non-linear polynomial equation based on a group of individuals having aggressive PCa and a group of individuals not having aggressive PCa.

18. The method of claim 1, wherein the at least 80 SNPpc comprise rs2297434, rs16860513, rs17138478, rs17832285, rs10993994, rs16902094, rs721048, rs888507, rs12475433, rs16901979, rs12947919, rs11649743, rs7106762, rs6545962, rs9364554, rs12151618, rs651164, rs11091768, rs10107982, rs385894, rs2659051, rs7213769, rs12946864, rs1873555, rs12793759, rs17467139, rs2710647, rs4871779, rs13265330, rs5945619, rs2660753, rs902774, rs6794467, rs4699312, rs7141529, rs5918762, rs1894292, rs6579002, rs11568818, rs7818556, rs9830294, rs9911515, rs620861, rs2018334, rs6062509, rs9457937, rs17021918, rs758643, rs2331780, rs10896437, rs12500426, rs16901922, rs9297746, rs2647262, rs7102758, rs10807843, rs7679673, rs12543663, rs138213197, rs1009, rs2735839, rs1933488, rs3120137, rs17224342, rs747745, rs684232, rs10086908, rs3765065, rs1016343, rs2107131, rs3771570, rs2838053, rs11672691, rs2047408, rs6983267, rs1992833, rs2028900, rs2315654, rs2132276, and rs3019779.

19. A method for determining aggressive prostate cancer (PCa) markers in an individual, comprising the steps of:
(i) Providing at least one biological sample from said individual;
(ii) Contacting the biological sample with an assay device comprising a first category of ligands which bind specifically to at least three kallikrein family protein PCa biomarkers, the first category of ligands including a plurality of different ligands binding specifically to each of the at least three kallikrein family protein PCa biomarkers, wherein the at least three PCa biomarkers include at least one of PSA, intact PSA (iPSA), total PSA (tPSA), free PSA (fPSA), and hK2;
(iii) Contacting the biological sample with an assay device comprising a solid phase having immobilised thereon a second category of ligands which bind specifically to at least 80 SNPs related to PCa (SNPpc), the second category of ligands including a plurality of different ligands binding specifically to each of said SNPpc, wherein
(a) said at least 80 SNPpc are selected from the group consisting of rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573; or (b) wherein said at least 80 SNPpc are selected from the group consisting of 657del5, rs10086908, rs1016343, rs10187424, rs1041449, rs10486567, rs1054564, rs10875943, rs10896449, rs10934853, rs10993994, rs11067228, rs11135910, rs11228565, rs11568818, rs11649743, rs11650494, rs11672691, rs11704416, rs12130132, rs12409639, rs12418451, rs12500426, rs12543663, rs12621278, rs12653946, rs1270884, rs130067, rs13252298, rs13385191, rs1354774, rs1363120, rs137853007, rs138213197, rs1447295, rs1465618, rs1512268, rs1571801, rs16901979, rs16902094, rs17021918, rs17632542, rs17879961, rs1859962, rs1894292, rs1933488, rs1983891, rs2018334, rs2121875, rs2242652, rs2273669, rs2292884, rs2405942, rs2660753, rs2735839, rs2736098, rs2928679, rs3213764, rs339331, rs3771570, rs3850699, rs3863641, rs401681, rs4245739, rs4430796, rs445114, rs4643253, rs4857841, rs4962416, rs5759167, rs5919432, rs5945619, rs6062509, rs620861, rs6465657, rs6763931, rs684232, rs6869841, rs6983267, rs6983561, rs7127900, rs7210100, rs721048, rs7241993, rs7611694, rs7679673, rs7931342, rs8008270, rs8102476, rs888663, rs902774, rs9364554, rs9600079, and rs9623117; and (iv) Measuring
   a. a presence or concentration of each of said PCa biomarkers binding the ligands in said first category; and
   b. a presence or absence of each of said SNPpc binding the ligands in said second category.

\* \* \* \* \*

UNITED STATES PATENT AND TRADEMARK OFFICE
CERTIFICATE OF CORRECTION

PATENT NO. : 10,431,326 B2  
APPLICATION NO. : 14/443970  
DATED : October 1, 2019  
INVENTOR(S) : Henrik Grönberg et al.

Page 1 of 1

It is certified that error appears in the above-identified patent and that said Letters Patent is hereby corrected as shown below:

On the Title Page

Item (30), change "1251312" to --1251312-3--.

Item (30), change "1350600" to --1350600-1--.

In the Claims

Claim 14, Column 34, Line 47, change "rs48331039" to --rs4833103--.

Signed and Sealed this
Seventh Day of January, 2020

Andrei Iancu
*Director of the United States Patent and Trademark Office*